United States Patent
Cook et al.

(10) Patent No.: US 11,517,352 B1
(45) Date of Patent: Dec. 6, 2022

(54) DEVICE AND TREATMENT OF ABNORMAL SPINE CURVATURE

(71) Applicant: Gomboc, LLC, Metairie, LA (US)

(72) Inventors: Stephen D. Cook, Metairie, LA (US); Liam P. Nolan, New Orleans, LA (US); Laura P. Patron, Belle Chase, LA (US)

(73) Assignee: Gomboc, LLC, Metairie, LA (US)

( * ) Notice: Subject to any disclaimer, the term of this patent is extended or adjusted under 35 U.S.C. 154(b) by 0 days.

(21) Appl. No.: 17/355,163

(22) Filed: Jun. 22, 2021

(51) Int. Cl.
*A61B 17/88* (2006.01)
*A61B 17/70* (2006.01)
*A61B 17/00* (2006.01)

(52) U.S. Cl.
CPC ...... *A61B 17/7001* (2013.01); *A61B 17/7082* (2013.01); *A61B 2017/00876* (2013.01)

(58) Field of Classification Search
CPC ............ A61B 17/7001; A61B 17/7082; A61B 2017/00876
USPC ....... 606/246, 257, 259, 260, 261, 264, 265, 606/266, 267, 270, 275, 278, 279, 300, 606/305, 308, 309, 315, 323, 328, 331, 606/90, 105
See application file for complete search history.

(56) References Cited

U.S. PATENT DOCUMENTS

| | | | |
|---|---|---|---|
| 10,555,787 B2 * | 2/2020 | Cook | A61B 34/73 |
| 2003/0195633 A1 * | 10/2003 | Hyde, Jr. | A61F 2/40 623/18.12 |
| 2009/0048618 A1 * | 2/2009 | Harrison | A61B 17/70 606/153 |
| 2014/0296919 A1 * | 10/2014 | Culbert | A61B 17/8685 606/272 |
| 2017/0231663 A1 * | 8/2017 | Hammann | A61B 17/7016 606/258 |
| 2018/0014838 A1 * | 1/2018 | Ning | A61B 17/7023 |
| 2019/0070426 A1 * | 3/2019 | Alam | A61N 2/06 |
| 2020/0330256 A1 * | 10/2020 | Archbold | A61B 17/86 |

* cited by examiner

*Primary Examiner* — Eduardo C Robert
*Assistant Examiner* — David C Comstock
(74) *Attorney, Agent, or Firm* — Grimes & Yvon LLP

(57) ABSTRACT

A magnetic screw device that includes a fastening stem, a housing, a magnet assembly, and one or more magnets. The housing is configured to receive the fastening stem, such that the housing can rotate and angulate relative to the fastening stem. The housing is also configured to secure the magnet assembly. The magnet assembly contains two magnet holders that are each configured to receive one of the two magnets. The magnetic screw device can be used in a method of treating a spine with an abnormal curvature.

20 Claims, 9 Drawing Sheets

DEVICE AND TREATMENT OF ABNORMAL SPINE CURVATURE

FIELD OF INVENTION

The present invention generally relates to prosthetic devices and their use. In particular, the present invention relates to devices containing magnets for use in treating or preventing the progression of abnormal curvatures in the spine.

BACKGROUND OF THE INVENTION

The spine is comprised of vertebrae, along with cartilaginous discs between the vertebrae, which are stacked on top of each other to provide support to the body, maintain posture, and protect the spinal cord. A healthy spine typically has slight curvatures, which help absorb stress from body movement and gravity. However, abnormalities can occur, which misalign or exaggerate the curvature in certain areas of the spine.

There are a number of health problems and conditions that can cause the spine to curve more than normal or to be misaligned. For example, lordosis, also known as swayback, is an abnormality in which the spine significantly curves inward at the lower back or lumbar region. Kyphosis is a condition characterized by an abnormally rounded upper back, more than 50 degrees of curvature, and most commonly affects the elderly.

A third type of abnormal spinal curvature is scoliosis, which is a condition of the spine that primarily affects young adolescents—typically between the ages of 10 and full grown—and more often females than males. Scoliosis causes the spine to curve sideways, such that from an anterior or posterior view the spine resembles a letter "C" or "S" rather than a straight line. There are several types of scoliosis, including congenital, which develops before birth; neuromuscular, which may be caused by muscular dystrophy or cerebral palsy; and idiopathic, in which the cause of the curve is unknown and is the most common type.

While curves less than 25 degrees (as determined using the Cobb method of measuring the degree of scoliosis) are typically monitored for progression of the deformity, curves greater than 25 degrees are considered serious enough to require treatment. Curves 25 to 45 degrees in a growing child are most often treated using braces in an attempt to stabilize the spine and prevent further curve progression that would require surgery. However, bracing does not straighten the spine, and its efficacy in stabilizing the spine varies; in the United States, it is successful in preventing curve progression in as many as 30,000 cases each year, but unsuccessful in about 40,000 cases. Curves greater than 45 degrees or those continuing to progress with bracing may require fusion surgery.

Fusion surgery involves the attachment of metal rods and screws, wires, and/or hooks to the spine using bone graft material in order to straighten the spine and fuse the vertebrae together. However, the surgery can require a long recovery time and has a risk of neurologic complications and infection. In addition, fusion surgery may fail to reduce the pain caused by spinal curvature, and may lead to further spine degradation and curve changes.

Thus, there remains a need in the art in patients with abnormal spine curvature, especially for patients with scoliosis, for an intervention that effectively straightens and stabilizes the spine, and/or prevents further curve progression.

SUMMARY OF INVENTION

Some of the main aspects of the present invention are summarized below. Additional aspects are described in the Detailed Description of the Invention, Examples, Drawings, and Claims sections of this disclosure. The description in each section of this disclosure is intended to be read in conjunction with the other sections. Furthermore, the various embodiments described in each section of this disclosure can be combined in various different ways, and all such combinations are intended to fall within the scope of the present invention.

The invention provides a device and methods for treating abnormal spine curvatures.

In one aspect, the invention provides a magnetic screw device comprising a fastening stem, a housing, a magnet assembly, and one or more magnets. In embodiments of the invention, the magnetic screw device comprises two magnets.

The fastening stem comprises a first end, a second end, a shank therebetween, and a longitudinal axis therebetween, in which the first end comprises a spherical or part spherical surface, the second end comprises a taper to a pointed or approximately pointed shape, and the shank comprises a thread.

The housing comprises a top end, a bottom end, wall therebetween, and a bore between the top end and bottom end that defines an inner surface, in which a portion of the inner surface adjacent to the bottom end comprises a concave spherical or part-spherical surface that is configured to engage with the spherical or part-spherical surface of the first end of the fastening stem. The housing also comprises a first slot and a second slot that extends from the top end towards the bottom end and is located on opposing sites of the wall.

The magnet assembly comprises a shaft, a magnet holder on one or both ends of the shaft, a removable holder cap for each magnet holder, and a longitudinal axis extending between the ends of the shaft. Each magnet holder comprises an outer surface, a bore defining an inner surface, a closed end, and an open end. Each holder cap is configured to enclose the open end of the magnet holder. Further, the shaft of the magnet assembly is removably received by the first slot and second slot of the housing.

Each magnet of the magnetic screw device is configured to be received by one of the magnet holders.

In some embodiments, the thread of the shank is single-lead. In other embodiments, the thread of the shank is multiple-lead, such as double-lead or triple-lead.

In some embodiments, the first end of the fastening stem comprises a drive on its surface, in which the drive is configured to receive a driver.

In some embodiments, the engagement of the portion of the inner surface having a concave spherical or part-spherical surface with the spherical or part-spherical surface of the first end of the fastening stem permits the housing to rotate up to 360 degrees. In certain embodiments, the engagement of the portion of the inner surface having a concave spherical or part-spherical surface with the spherical or part-spherical surface of the first end of the fastening stem permits the housing to tilt in the range of about 50 to about 100 degrees relative to the longitudinal axis of the fastening stem.

In some embodiments, the first slot and second slot of the housing comprises a shape of a rectangle having a rounded end.

In some embodiments, the holder cap is adhered to the magnet holder by a locking mechanism. In certain embodiments, the locking mechanism is selected from a locking nut, thread, taper lock, screw, and press fit.

In some embodiments, the magnet assembly further comprises a sleeve at each end of the shaft; and, when a magnet holder is also present at the end of the shaft, the sleeve is between the magnet holder and the shaft. In certain embodiments, each sleeve is positioned such that it is adjacent to one of the first slot or the second slot when the shaft is received by the first slot and second slot.

In some embodiments, the housing further comprises a securing cap that is configured to engage with the housing at its top end via a locking mechanism. In certain embodiments, the locking mechanism of the securing cap is selected from thread, taper lock, and press fit.

In some embodiments, the engagement of the securing cap with the housing secures the magnet assembly within the housing. In certain embodiments, the engagement of the securing cap with the housing secures the magnet assembly within the housing and prevents rotational and angular movement of the housing relative to the fastening stem.

In some embodiments, the magnets comprise a material that is iron-based, nickel-based, cobalt-based, or an alloy of rare-earth metals. In certain embodiments, the magnets comprise an alloy of neodymium, iron, and boron.

In some embodiments, the magnets in each of the magnet holders have the same polarity. In other embodiments, the magnets in each of the magnet holders have different polarities.

In another aspect, the invention provides a magnetic screw system comprising two or more of the magnetic screw devices.

In yet another aspect, the invention provides methods involving the magnetic screw devices. Some embodiments relate to a method of treating a spine with an abnormal curvature in a subject in need thereof, the method comprising implanting one or more of the magnetic screw devices into each of two or more vertebrae at the curvature and/or adjacent to the abnormal curvature. Some embodiments relate to a method of stabilizing a spine with an abnormal curvature in a subject in need thereof, the method comprising implanting one or more of the magnetic screw devices into each of two or more vertebrae at the curvature and/or adjacent to the abnormal curvature. Some embodiments relate to a method of correcting an abnormal curvature in a spine over time in a subject in need thereof, the method comprising implanting one or more of the magnetic screw devices into each of two or more vertebrae at the curvature and/or adjacent to the abnormal curvature. Some embodiments relate to a method of preventing curve progression of a spine with an abnormal curvature in a subject in need thereof, the method comprising implanting one or more of the magnetic screw devices into each of two or more vertebrae at the curvature and/or adjacent to the abnormal curvature. Some embodiments relate to a method of reducing the risk of curve progression of a spine with an abnormal curvature in a subject in need thereof, the method comprising implanting one or more of the magnetic screw devices into each of two or more vertebrae at the curvature and/or adjacent to the abnormal curvature. Some embodiments relate to a method of aligning vertebrae in a spine with an abnormal curvature in a subject in need thereof, the method comprising implanting one or more of the magnetic screw devices into each of two or more vertebrae at the curvature and/or adjacent to the abnormal curvature. Further, some embodiments relate to a method of aiding the realignment of a spine with an abnormal curvature in a subject in need thereof, the method comprising implanting one or more of the magnetic screw devices into each of two or more vertebrae at the curvature and/or adjacent to the abnormal curvature.

In some embodiments, the method comprises implanting the magnetic screw device into one of the pedicles of each of two or more vertebrae. In other embodiments, the method comprises implanting the magnetic screw device into both pedicles of each of two or more vertebrae.

In some embodiments, the method comprises orienting the housing such that the longitudinal axis of the magnet assembly is approximately parallel with the longitudinal axis of the spine. In other embodiments, the method comprises orienting the housing such that the longitudinal axis of the magnet assembly is angled relative to the longitudinal axis of the spine.

In certain embodiments, the method comprises orienting the housing such that the longitudinal axis of the magnet assembly is at an angle of about 5 degrees to about 60 degrees relative to the longitudinal axis of the spine.

In certain embodiments, the magnet on each magnetic screw device is oriented to have the same magnetic pole alignment.

In some embodiments, the method further comprises implanting one or more magnetic screw devices into two or more vertebrae that are adjacent to the vertebrae at the curvature.

In some embodiments, the method further comprises the subject wearing an external brace that comprises one or more magnets, wherein the one or more magnets in the external brace are oriented to have the same magnetic pole alignment as the one or more magnets of the implanted magnetic screw devices.

In a further aspect, the invention provides a kit comprising (a) two or more constructs, in which each construct comprises a fastening stem in connection with a housing; (b) two or more magnet assemblies; (c) two or more magnets; and (d) instructions on how to assemble magnetic screw devices from the constructs securing caps, magnet assemblies, and magnets; instructions on how to implant the magnetic screw devices into a subject; or a combination thereof. In some embodiments, the fastening stem comprises a first end, a second end, a shank therebetween, and a longitudinal axis therebetween, in which the first end comprises a spherical or part-spherical surface, the second end comprises a taper to a pointed or approximately pointed shape, and the shank comprises a thread. In some embodiments, the housing comprises a top end, a bottom end, a wall therebetween, and a bore between the top end and bottom end that defines an inner surface, in which a portion of the inner surface adjacent to the bottom end comprises a concave spherical or part-spherical surface that is configured to engage with the spherical or part-spherical surface of the first end of the fastening stem; and in which the housing comprises a first slot and a second slot that extends from the top end towards the bottom end and is located on opposing sites of the wall. In some embodiments, the magnet assembly comprises a shaft, a magnet holder on one of both ends of the shaft, and a removable holder cap for each magnet holder, in which each magnet holder comprises an outer surface, a bore defining an inner surface, a closed end, and an open end; in which each holder cap is configured to enclose the open end of the magnet holder; and in which the shaft of the magnet assembly is removably received by the first slot and second slot of the housing. In some embodiments, each magnet in the kit is configured to be received by one of the magnet holders.

BRIEF DESCRIPTION OF THE DRAWING FIGURES

The present disclosure will be further explained with reference to the attached drawing figures, wherein like structures are referred to by like numerals throughout the several views. The drawing figures shown are not necessarily to scale, with emphasis instead generally being placed upon illustrating the principles of the present disclosure, and some features may be exaggerated to show details of particular components. In addition, any measurements, specifications, and the like shown in the drawing figures, or described below, are intended to be illustrative, and not restrictive. Therefore, specific structural and functional details disclosed herein are not to be interpreted as limiting, but merely as a representative basis for teaching one skilled in the art to variously employ the devices of the present invention and methods of their use.

FIG. 1A shows a magnetic screw device in which a magnet holder is on both ends of the shaft of the magnet assembly, and FIG. 1B shows a magnetic screw device in which a magnet holder is on one end of the shaft of the magnet assembly.

Figure 7:
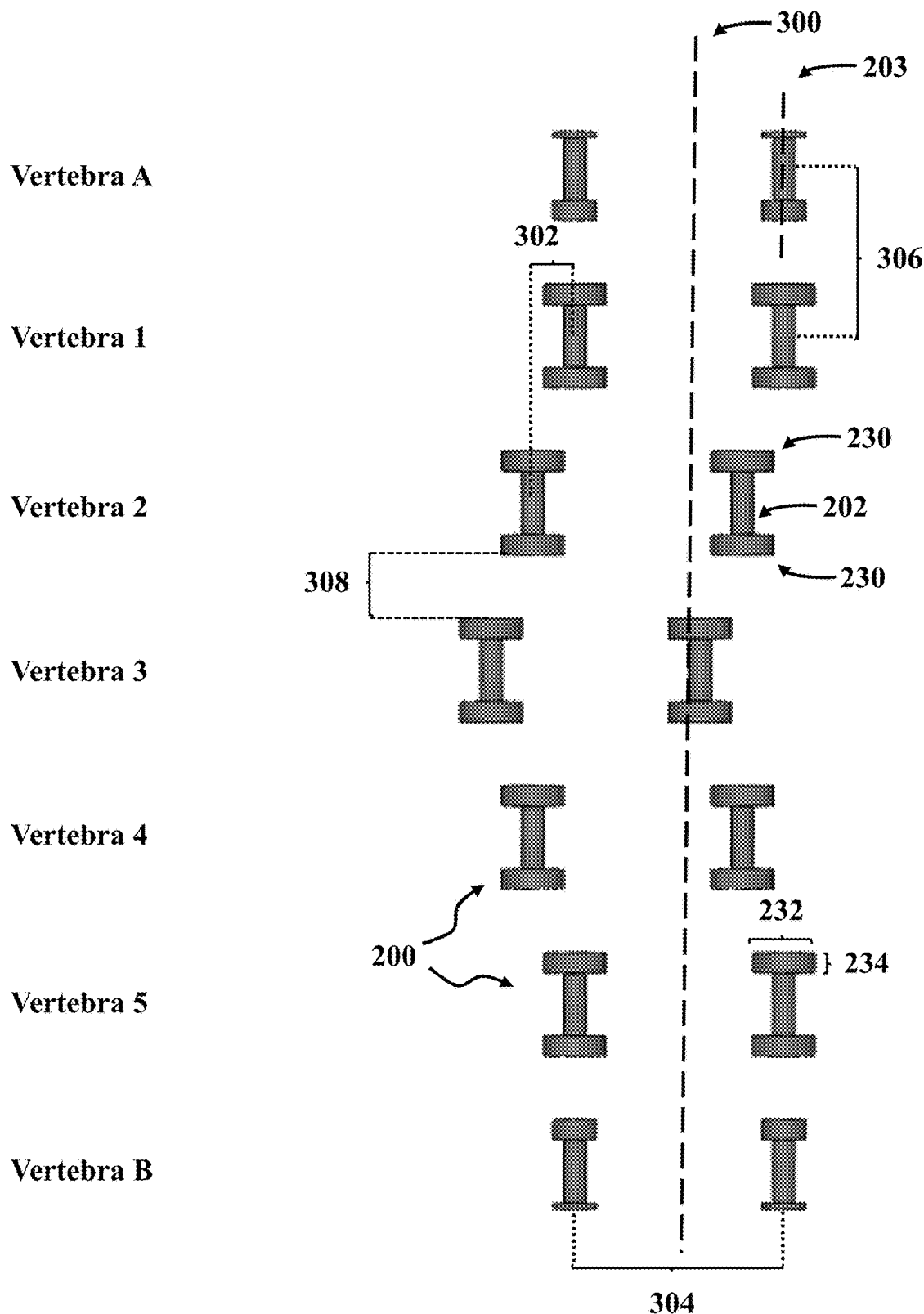

FIG. 7 shows a configuration of implanted magnetic screw devices (with only the magnet assemblies shown) relative to a 5-vertebrae-level abnormal C-type spinal curvature, in which the longitudinal axis of the magnet assemblies is parallel to the longitudinal axis of the spine, and in which the magnetic screw devices are implanted in the area of the curvature and above and below the curvature, according to embodiments of the present invention.

Figure 8:
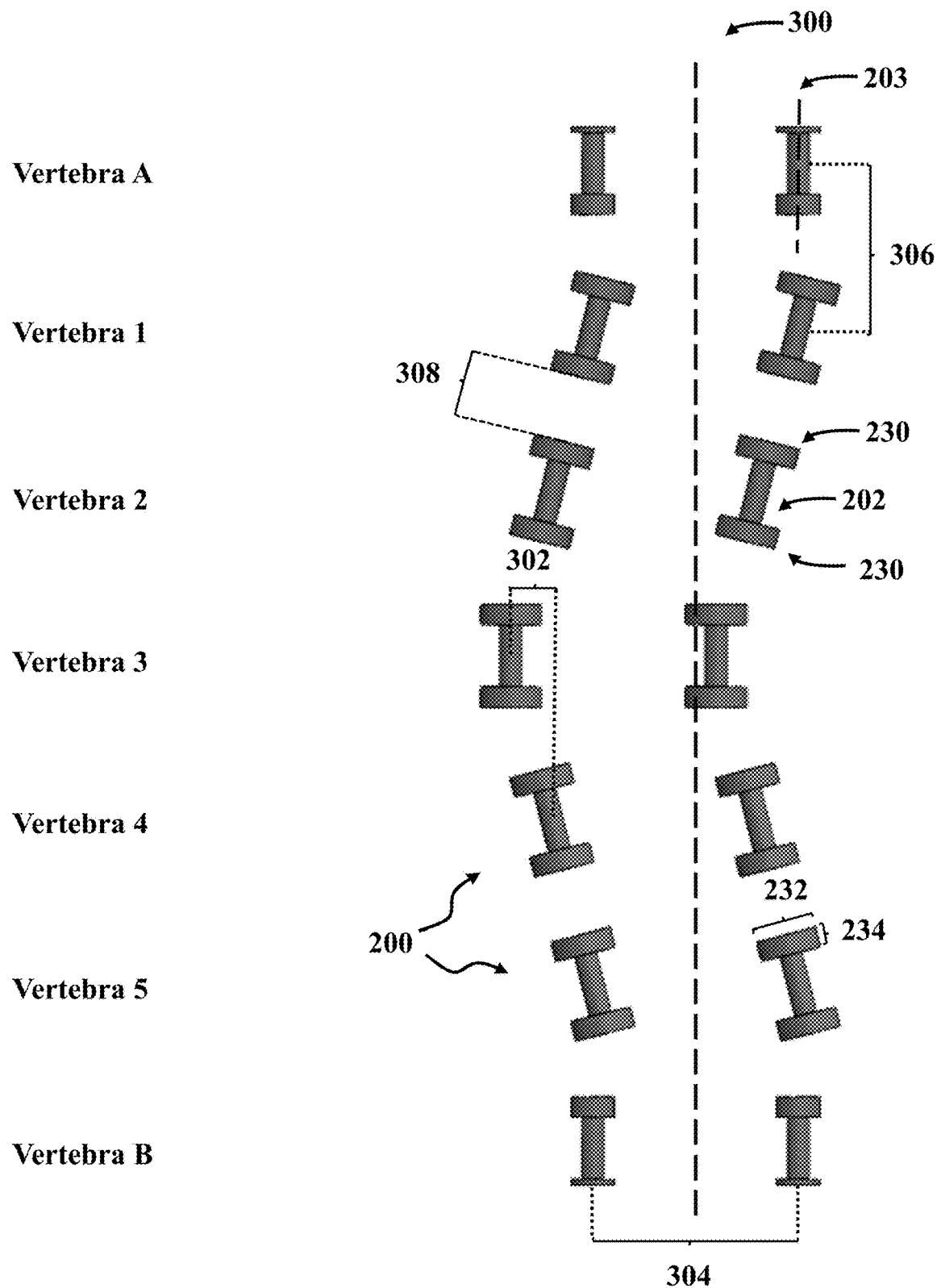

FIG. 8 shows a configuration of implanted magnetic screw devices (with only the magnet assemblies shown) relative to a 5-vertebrae-level abnormal C-type spinal curvature, in which the longitudinal axis of the magnet assemblies is angled relative to the longitudinal axis of the spine, and in which the magnetic screw devices are implanted in the area of the curvature and above and below the curvature, according to embodiments of the present invention.

DETAILED DESCRIPTION OF THE INVENTION

The practice of the present invention will employ, unless otherwise indicated, conventional techniques of biomechanics and mechanical engineering, biomaterials and material engineering, orthopaedics, biology, anatomy, and clinical practice, which are within the skill of the art.

In order that the present invention can be more readily understood, certain terms are first defined. Additional definitions are set forth throughout the disclosure. Unless defined otherwise, all technical and scientific terms used herein have the same meaning as commonly understood by one of ordinary skill in the art to which this invention is related.

Any headings provided herein are not limitations of the various aspects or embodiments of the invention, which can be had by reference to the specification as a whole. Accordingly, the terms defined immediately below are more fully defined by reference to the specification in its entirety.

All references cited in this disclosure are hereby incorporated by reference in their entireties. In addition, any manufacturers' instructions or catalogues for any products cited or mentioned herein are incorporated by reference. Documents incorporated by reference into this text, or any teachings therein, can be used in the practice of the present invention. Documents incorporated by reference into this text are not admitted to be prior art.

The description provided herein is given for clearness of understanding only, and no unnecessary limitations should be understood therefrom, as modifications within the scope of the invention may be apparent to those having ordinary skill in the art.

Detailed embodiments of the present methods and magnetic devices are disclosed herein; however, it is to be understood that the disclosed embodiments are merely illustrative and that the methods and magnetic devices may be embodied in various forms. In addition, each of the examples given in connection with the various embodiments of the systems and methods are intended to be illustrative, and not restrictive.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various steps may be changed without departing from the scope or spirit of the method, unless described otherwise. In addition, some of the individual steps can be combined, omitted, or further subdivided into additional steps.

The present invention relates to a magnetic screw system and its use in spines with abnormal curvature. The magnetic screw system comprises one or more magnetic screw devices, which, upon implantation into vertebrae of the spine, are oriented such that magnetic forces exist that compel the opposing poles of the magnets to align, and in turn exert a force that helps to straighten the curvature of the spine, resist those forces which tend to progress abnormal curvature over time, and/or maintain vertical alignment of the spine. Each magnetic screw device comprises one or more magnets, which advantageously permits the magnetic screw system to be more customizable and allows for different combinations of attractive and repulsive forces to occur between vertebrae.

The methods of the present invention provide advantages as compared to current treatments for abnormal spinal curvature. For example, as compared to other treatments such as fusion surgery, the methods of the present invention may be less invasive, which can lead to shorter recovery time; may have a lower risk of neurological complications; and may result in a smaller surgical scar. Another benefit of the present invention is that a brace will often not be required and, if used, would only provide additional assistance in spine stabilization and prevention of curve progression.

Definitions

The phraseology or terminology in this disclosure is for the purpose of description and not of limitation, such that the terminology or phraseology of the present specification is to be interpreted by the skilled artisan in light of the teachings and guidance.

As used in this specification and the appended claims, the singular forms "a," "an," and "the" include plural referents, unless the context clearly dictates otherwise. The terms "a" (or "an") as well as the terms "one or more" and "at least one" can be used interchangeably.

Furthermore, "and/or" is to be taken as specific disclosure of each of the two specified features or components with or without the other. Thus, the term "and/or" as used in a phrase such as "A and/or B" is intended to include A and B, A or B, A (alone), and B (alone). Likewise, the term "and/or" as used in a phrase such as "A, B, and/or C" is intended to include A, B, and C; A, B, or C; A or B; A or C; B or C; A and B; A and C; B and C; A (alone); B (alone); and C (alone).

Wherever embodiments are described with the language "comprising," otherwise analogous embodiments described in terms of "consisting of" and/or "consisting essentially of" are included.

Units, prefixes, and symbols are denoted in their Système International de Unites (SI) accepted form. Numeric ranges are inclusive of the numbers defining the range, and any individual value provided herein can serve as an endpoint for a range that includes other individual values provided herein. For example, a set of values such as 1, 2, 3, 8, 9, and 10 is also a disclosure of a range of numbers from 1-10, from 1-8, from 3-9, and so forth. Likewise, a disclosed range is a disclosure of each individual value encompassed by the range. For example, a stated range of 5-10 is also a disclosure of 5, 6, 7, 8, 9, and 10.

A "subject" or "individual" or "patient" is any subject, particularly a mammalian subject, for whom diagnosis, prognosis, or therapy is desired. Mammalian subjects include humans, domestic animals, farm animals, sports animals, and laboratory animals including, e.g., humans, non-human primates, canines, felines, porcines, bovines, equines, rodents, including rats and mice, rabbits, etc.

As used herein, the terms "treating" and "treatment" refer to reduction in severity and/or frequency of symptoms, elimination of symptoms and/or underlying cause, prevention of the occurrence of symptoms and/or their underlying cause, and improvement or remediation of damage.

As used herein, the term "reduce" or "reducing" is used to refer to any decrease in occurrence or activity or degree thereof, including full blocking of the occurrence or activity.

As used herein, the term "correct" or "correcting" is used to refer to a mend or repair, either partially or fully, of a condition that, based on standard medical practices, requires or suggests mending or repair.

As used herein, the term "align" or "aligning" is used to refer to a physical change to an intended different position, including a position that is acceptable based on standard medical practices. "Align" or "aligning" does not require that the different position be linear.

As used herein, the term "aid" or "aiding" is used to refer to a decrease or increase in occurrence or activity or degree thereof due to an intervention (such as a therapy or, more relevantly, implantation of a magnetic screw device of the present invention), such that the decrease or increase is greater with the intervention than without the intervention.

Magnetic Screw System

An aspect of the invention relates to a magnetic screw system that comprises one or more magnetic screw devices.

Embodiments of the magnetic screw device of the present invention are shown in FIGS. 1-4. The magnetic screw device 100 may comprise a fastening stem 105, a housing 150, a magnet assembly 200, and at least one magnet 230. The fastening stem 105 may comprise a first end 106 that is configured to engage with the housing 150, a second end 107 that comprises a taper to a pointed or approximately pointed shape, a shank 108 therebetween, and a longitudinal axis 110 that extends between the first end 106 and the second end 107 and through the center of the cross-section of the fastening stem 105. In some embodiments, the shank 108 or portions thereof may comprise a taper towards the second end 107 (not shown).

The shank 108 may comprise a thread 112 that is configured to engage with bone and may extend the entire shank 108 or a portion thereof. In some embodiments, the thread 112 is a single-lead thread. In other embodiments, the thread 112 is a multiple-lead thread, such as a double-lead thread, a triple-lead thread, or a quadruple-lead thread. In certain embodiments, the thread 112 may have a pitch, depth, and shape that are known in the art for threads of orthopaedic screws, including cortical and/or cancellous screws. For example, the thread 112 may have any shape as known in the art for drilling into bone, including but not limited to, V-thread, buttress thread, reverse buttress, and square thread.

The fastening stem 105 may comprise a length and diameter appropriate for insertion into bone, preferably in a vertebra, more preferably into a pedicle of a vertebra. In some embodiments, the fastening stem 105 may comprise a length of about 20 mm to about 100 mm, or about 25 mm to about 80 mm. In some embodiments, the fastening stem 105 may comprise a width of about 3 mm to about 12 mm, or about 4 mm to about 10 mm, or about 4.5 mm to about 9.5 mm.

The first end 106 may comprise a spherical or part-spherical surface 114. In addition, a recess 116 may be provided on the first end 106 that is configured to receive a tool (not shown) that can apply a force, such as torque, to the fastener stem 105 and turn the thread 112 into bone. For example, the recess 116 may be a drive that is configured for insertion of a driver, such as a hex driver, Philips-head driver, flat-head driver, etc.

In some embodiments, the fastening stem 105 may include an external textured surface (not shown), which enhances fixation of the fastening stem 105 in bone and to aid in screw-bone interface stability. According to certain embodiments, plasma coating of a metal or ceramic may be applied to fastening stem 105 to create the external textured surface.

As shown in FIGS. 1-4, the housing 150 interconnects the magnet assembly 200 and the fastening stem 105. The housing 150 may have a shape approximating a cylinder or truncated cone, comprising a top end 152, a bottom end 154, a wall 156 therebetween, and a bore 158 between the top end 152 and bottom end 154 that defines an inner surface 160. The bottom end 154 is configured to receive the fastening stem 105. In some embodiments, a portion of the inner surface 160 adjacent to the bottom end 154 may comprise a concave spherical or part-spherical surface 162, which engages with the spherical or part-spherical surface 114 of the first end 106 of the fastening stem 105. The engagement between the concave spherical or part-spherical surface 162 of the inner surface 160 with the spherical or part-spherical surface 114 of the first end 106 of the fastening stem 105 can permit the housing 150 to rotate, for example, up to 360 degrees, and tilt, for instance, in the range of about 50 to about 100 degrees (about 25 to about 50 degrees in each direction) or about 60 to about 80 degrees (about 30 to about 40 degrees in each direction), relative to the longitudinal axis 110 of the fastening stem 105.

Figure 1A:
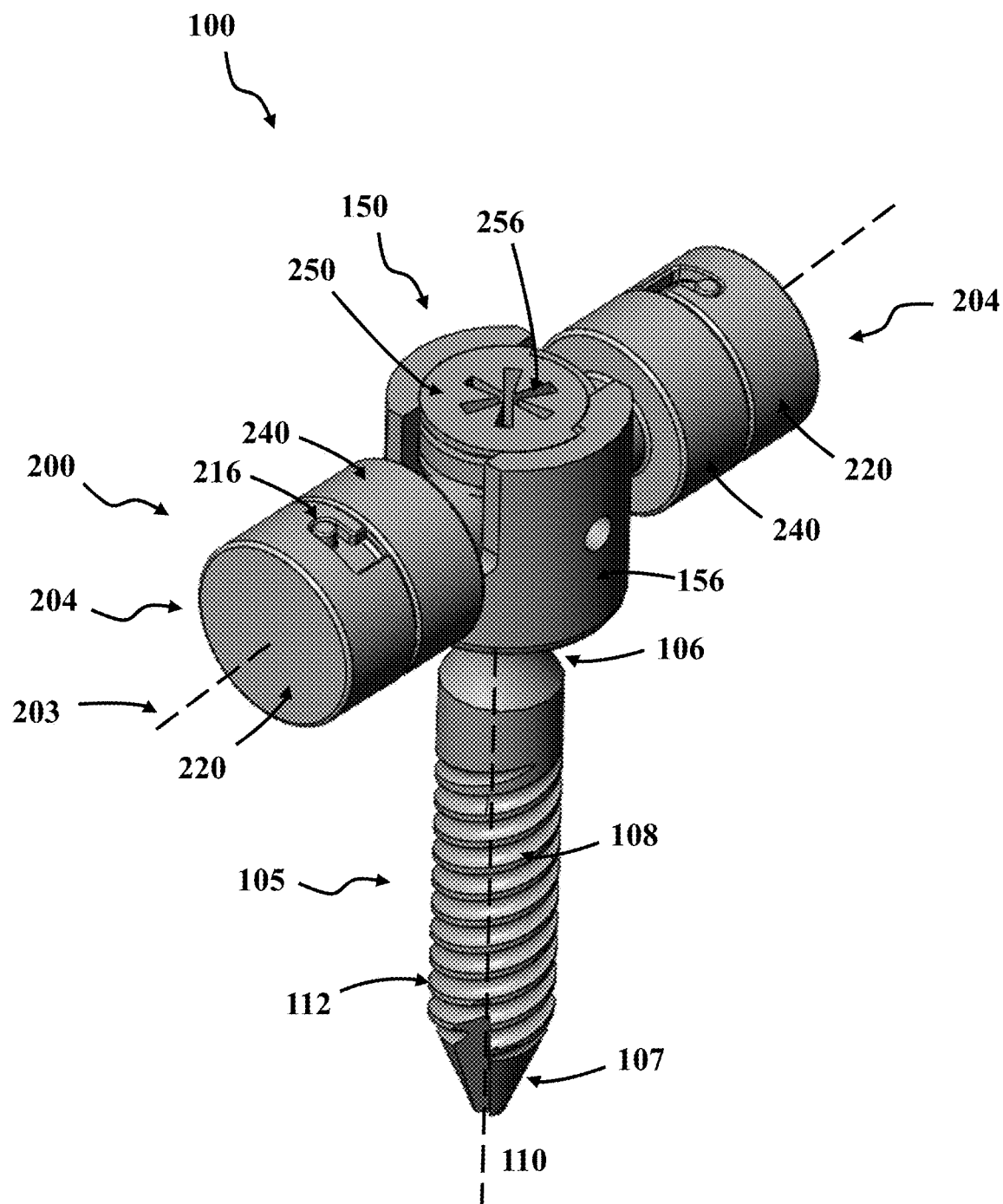
FIGS. 1A-1B are perspective views of magnetic screw devices according to embodiments of the present invention.
Figure 1B:
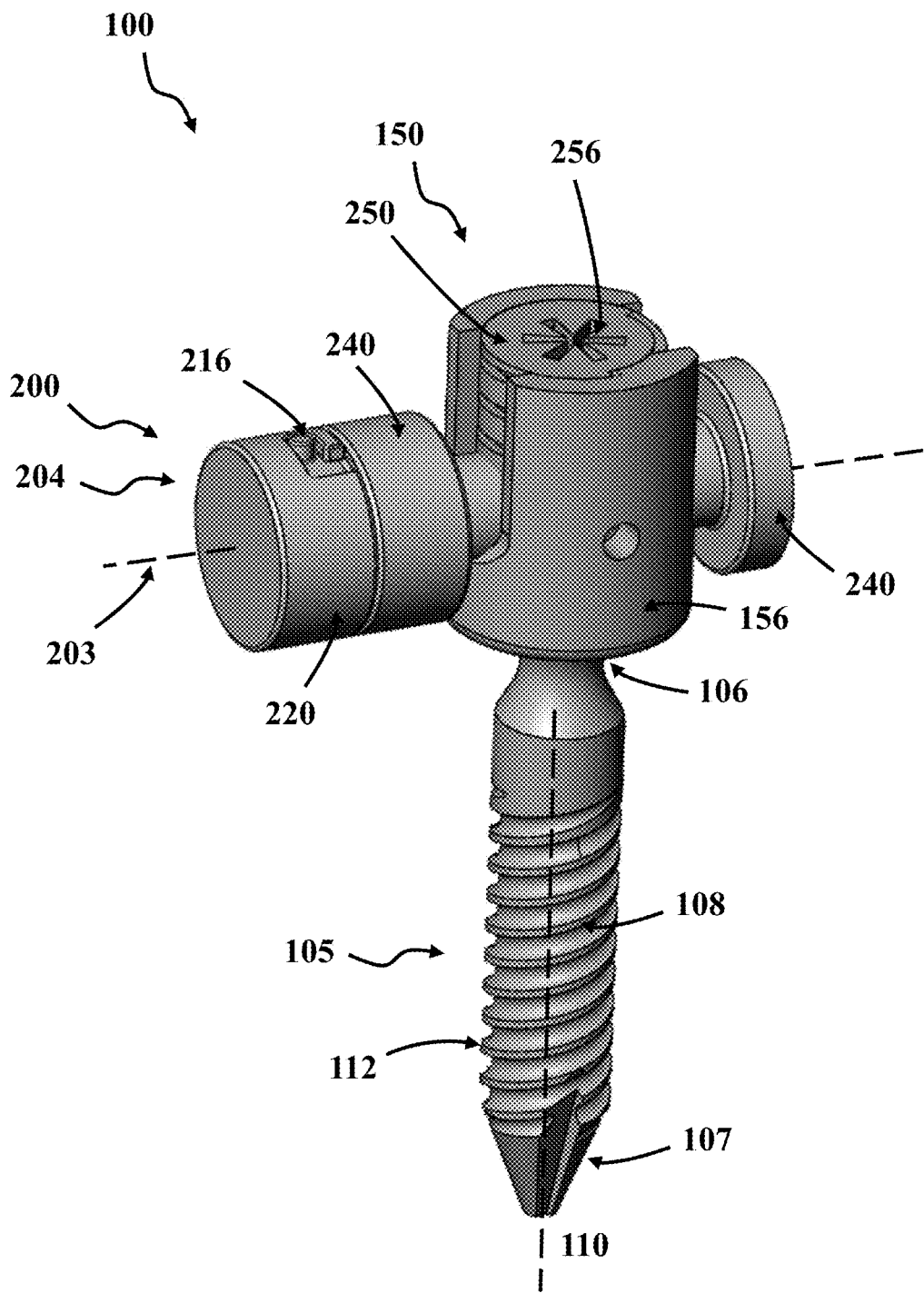
Figure 2:
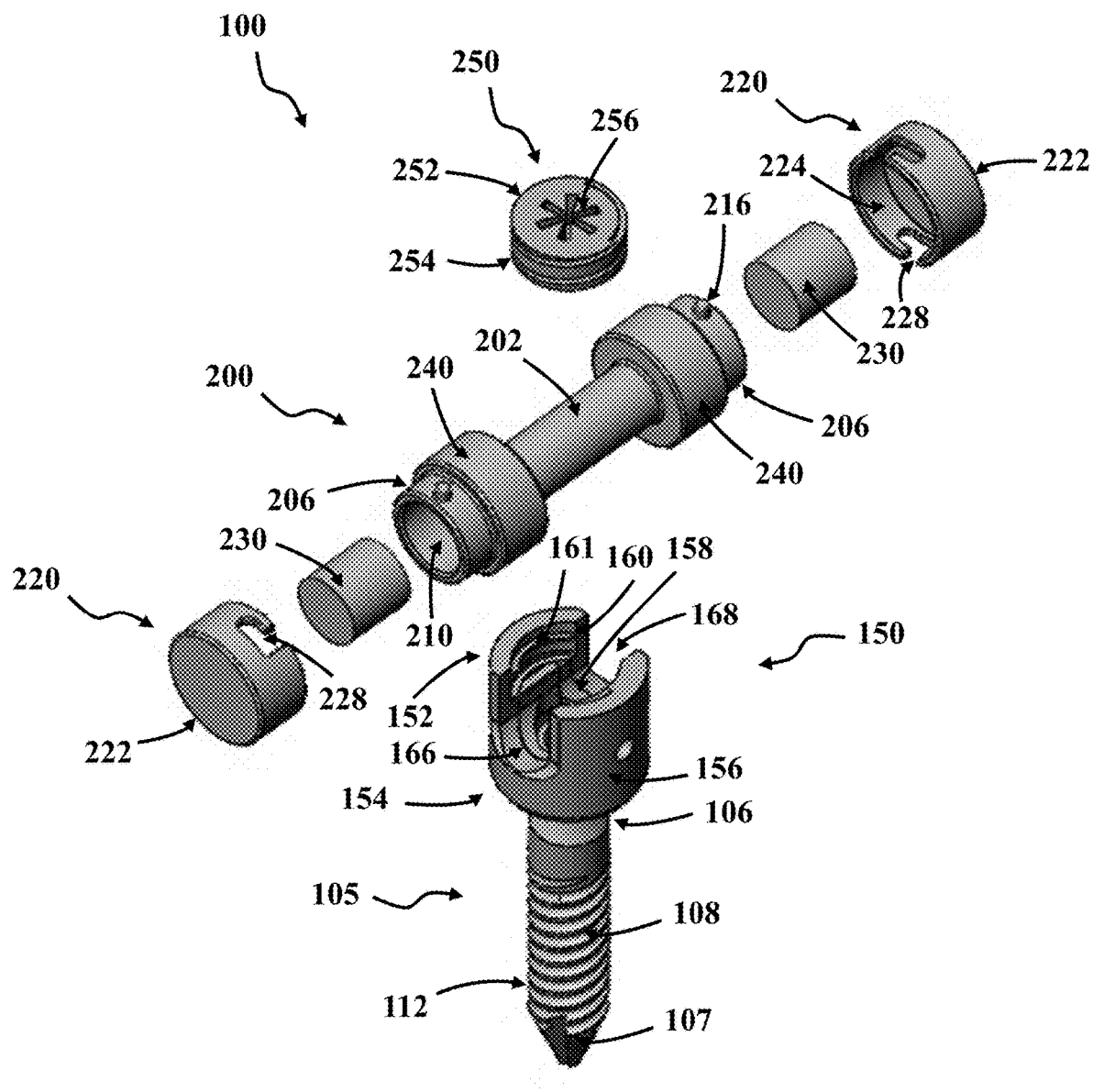
FIG. 2 is an exploded view of a magnetic screw device according to embodiments of the present invention, in which a magnet holder is on both ends of the shaft of the magnet assembly.
Figure 3:
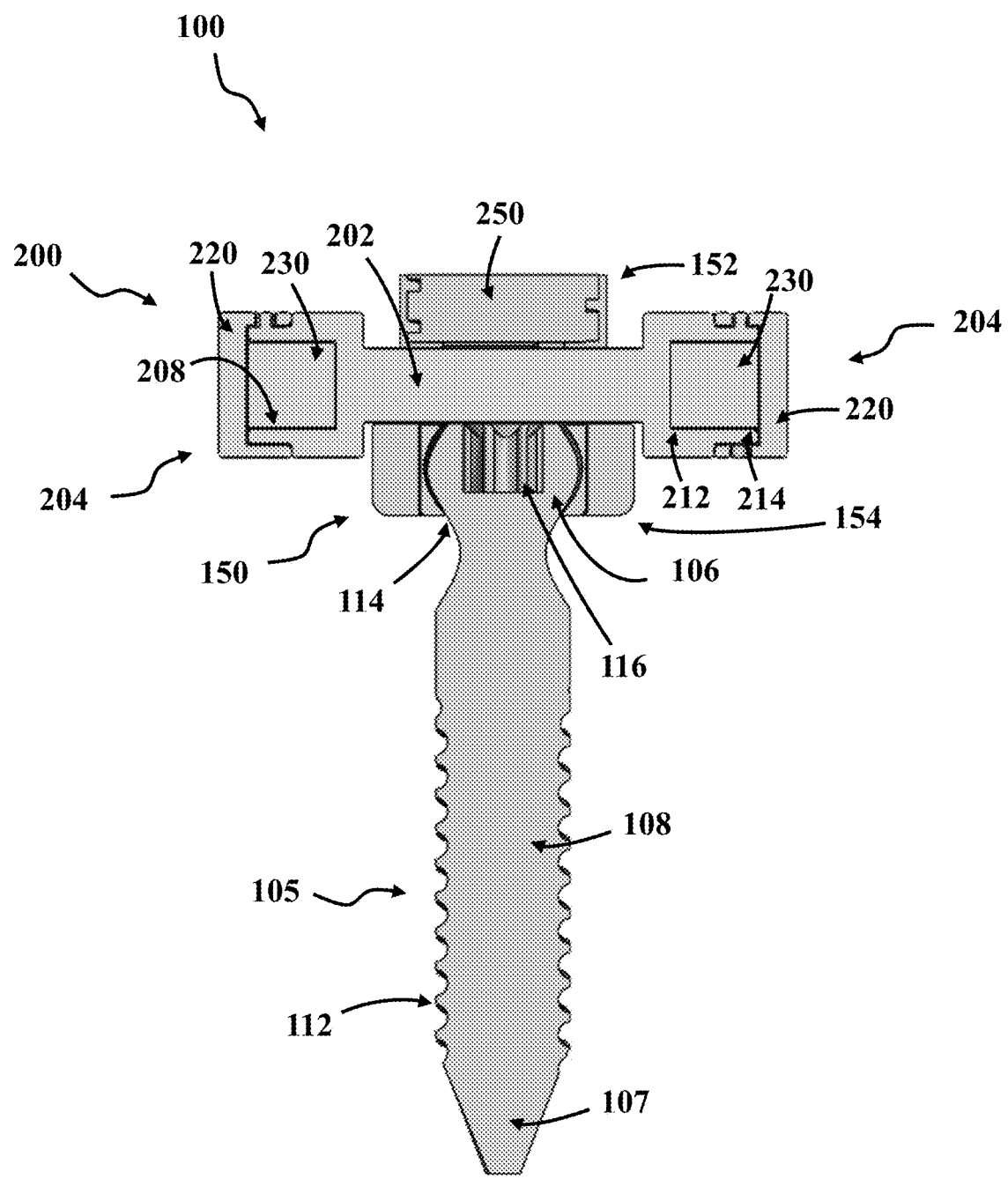
FIG. 3 is a cut-away view of a magnetic screw device according to embodiments of the present invention, in which a magnet holder is on both ends of the shaft of the magnet assembly.
Figure 4:
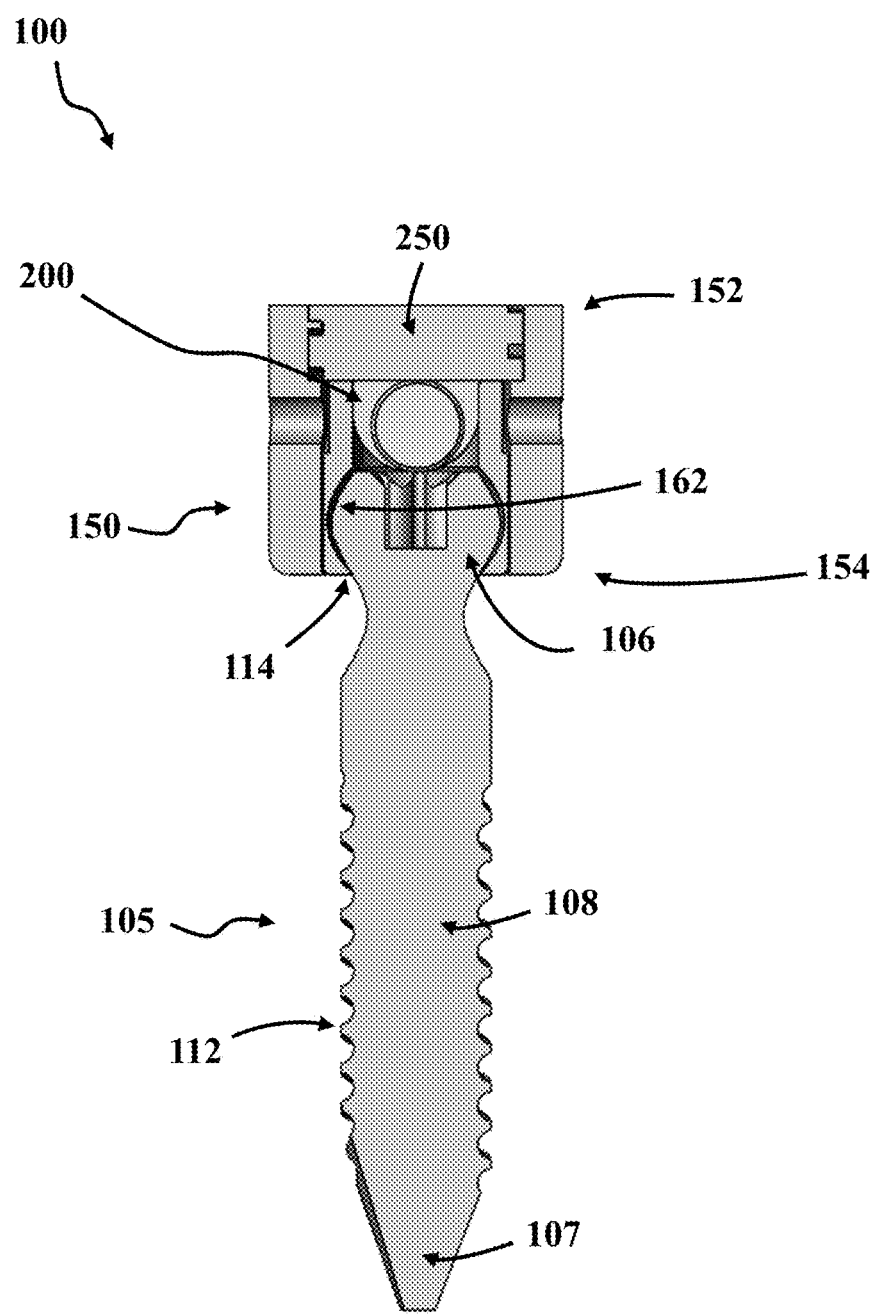
FIG. 4 is a cut-away view of a magnetic screw device according to embodiments of the present invention, in which the view is rotated 90 degrees about the longitudinal axis from the view of FIG. 3.

In some embodiments, the housing 150 comprises a first slot 166 and a second slot 168 in the wall 156 that extends from the top end 152 (see FIGS. 1 and 2). The first slot 166 and second slot 168 may be located on opposing sites of the wall 156. The slots are configured to receive the magnet assembly 200. In some embodiments, each slot comprises a shape of a rectangle, in which the side nearest the enclosed end 154 of the housing 150 is rounded or hemispherical.

The magnet assembly 200 comprises a shaft 202, a magnet holder 204 on both (see FIG. 1A) or one (see FIG. 1B) ends of the shaft 202, and a longitudinal axis 203 that extends between the ends of the shaft 202 and through the center of the cross-section of the shaft 202. The magnet holder 204 may comprise an outer surface 206 and a bore 210 defining an inner surface 208, an enclosed end 212 and an open end 214. The bore 210 of each magnet holder 204 is configured to receive a magnet 230. The magnet assembly 200 comprises a means to enclose the magnet 230 within each bore 210, for example a holder cap 220 that comprises an outer surface 222 and an inner surface 224. The holder cap 220 may be secured to each magnet holder 204 by a locking mechanism. Examples of a locking mechanism may include, but is not limited to, a locking nut (e.g., a nut 216 on the outer surface 206 of the magnet holder 204 that engages with a slot 228 on the holder cap 220) (see FIGS. 1A, 1B, and 2), thread (e.g., a thread on the outer surface 222 of the holder cap 220 that engage with a corresponding thread on the inner surface 208 of the magnet holder 204, or a thread on the inner surface 224 of the holder cap 220 that engage with a corresponding thread on the outer surface 206 of the magnet holder 204) (not shown), taper lock (not shown), a screw (not shown), and press fit (not shown). In alternative embodiments, an adhesive may be used to secure the holder cap 220 onto the magnet holder 204.

The shaft 202 and the magnet holder 204 may comprise a shape of, or approximately of, a sphere, cylinder, hollow cylinder, ellipsoid, prism (e.g., cube, rectangular prism, triangular prism, pentagonal prism, hexagonal prism, etc.), hollow prism, pyramid, cone, torus, or other three-dimensional shapes known in the art. In preferred embodiments, the shaft 202 and the magnet holder 204 comprise a shape of, or approximately of, a cylinder.

The shaft 202 comprises a width or diameter that can be received by the first slot 166 and the second slot 168 of the housing 150. The shaft 202 also comprises a length that can at least accommodate the distance between the first slot 166 and the second slot 168 of the housing 150, but can vary based on the anatomical dimensions of the vertebra and the distance desired between the magnetic screw devices 100 once implanted into adjacent vertebrae. In general, the diameter or width of the shaft 202 is about 2 mm to about 10 mm, or about 3 mm to about 8 mm, and the length of the shaft 202 is about 5 mm to about 40 mm, or about 8 mm to about 30 mm.

The magnet holder 204 may comprise a width or diameter that is the same as the width or diameter of the shaft 202, or the magnet holder 204 may comprise a width or diameter that is different than the width or diameter of the shaft 202, i.e., the magnet holder 204 may have a greater or smaller width or diameter than the width or diameter of the shaft 202. Preferably, the width or diameter of the magnet holder 204 is greater than the width or diameter of the shaft 202. In general, the width or diameter of the magnet holder 204 is about 2 mm to about 25 mm, or about 3 mm to about 20 mm; and the length of the magnet holder 204 is about 4 mm to about 25 mm, or about 5 mm to about 20 mm.

The bore 210 of the magnet holder 204 and the magnet 230 that is received by the bore 210 may comprise a shape that of, or approximately of, a sphere, cylinder, hollow cylinder, ellipsoid, prism (e.g., cube, rectangular prism, triangular prism, pentagonal prism, hexagonal prism, etc.), hollow prism, pyramid, cone, torus, or other three-dimensional shapes known in the art. In preferred embodiments, the bore 210 and the magnet 230 are cylindrical or approximately cylindrical. The size of the bore 210 of the magnet holder 204 may vary in accordance with different magnet sizes. In general, the bore 210 may comprise a width or diameter of about 1 mm to about 25 mm, or about 2 mm to about 20 mm; and a length of about 3 mm to about 25 mm, or about 4 mm to about 20 mm.

In some embodiments, the magnet assembly 200 may comprise a sleeve 240 at one or both ends of the shaft 202. In embodiments in which a magnet holder 204 is on the end of the shaft 202, the sleeve 240 is between the magnet holder 204 and the shaft 202 (see FIGS. 1A and 1B). The sleeve 240 may be positioned to be adjacent to the first slot 166 and second slot 168 when the shaft 202 is received by the first slot 166 and second slot 168, as shown in FIG. 2. The sleeve 240 may help provide stabilize the magnet assembly 200 within the housing 150, and in particular may help prevent the magnet assembly 200 from moving in the direction of the longitudinal axis 203 of the magnet assembly 200. The width or diameter of the sleeve 240 may be greater than the width or diameter of the magnet holder 204 and the width or diameter of the shaft 202. In general, the width or diameter of the sleeve 240 is about 3 mm to 30 mm, or about 4 mm to about 20 mm; and the length of the sleeve 240 is about 4 mm to about 25 mm, or about 5 mm to about 20 mm.

The housing 150 may further comprise a securing cap 250 that comprises an outer surface 252. The securing cap 250 can engage with the housing 150 via a locking mechanism to secure the magnet assembly 200 within the housing 150. Examples of locking mechanisms may include, but are not limited to, a thread 254 (e.g., a thread 254 on the outer surface 252 of the securing cap 250 that engage with a corresponding thread 161 on the inner surface 160 of the wall 156 of the housing 150 near its top end 152) (see FIGS. 2-4), taper lock (not shown), and press fit (not shown). The securing cap 250 may also comprise a drive 256 on its top surface that is configured for insertion of a driver, such as a hex driver, Philips-head driver, flat-head driver, etc.

In some embodiments, the securing cap 250 may be configured to also function as a locking mechanism that can set the housing 150 at a rotation and/or angulation relative to the fastening stem 105. In such embodiments, the securing cap 250 may interact with the housing 150 to achieve one of two types of engagement: (i) a securing engagement, in which the magnet assembly 200 is secured to the housing 150; (ii), or a locking engagement, in which the magnet assembly 200 is secured to the housing 150 and the housing 150 is set to a rotation and/or angulation relative to the fastening stem 105. The change from a securing engagement to a locking engagement may occur by tightening the securing cap 250 to a further extent with the housing 150.

The magnet 230 of the magnetic screw device 100 may comprise materials known in the art. For example, the magnets 230 may be iron-based, nickel-based, cobalt-based, or an alloy of rare-earth metals. In certain embodiments, the magnets 230 may be a rare-earth magnet, which generally has strong attraction and repulsion forces and have high retentive capacity and resistance to demagnification. In preferred embodiments, the rare-earth magnet is an alloy of neodymium, iron, and boron ("NdFeB"). NdFeB magnets provide strong permanent magnetism, high retentive capacity, and resistance to demagnetization. In further preferred embodiments, the NdFeB magnets is N52 grade.

The polarity of the magnets 230 within the magnet holders may vary, depending on the forces that are intended to be generated once magnetic screw devices 100 are implanted. For example, the magnet 230 in each of the magnet holders may have the same polarity, or may have different polarities.

The fastening stem 105, housing 150, and magnet assembly 200 may comprise materials that are biocompatible to implantation into the body, preferably for orthopaedic applications. Examples of such materials include, but are not limited to, titanium, titanium alloy, cobalt chromium alloy, stainless steel, and a combination thereof. In some embodiments, the shaft 202 and the magnet holder 204, and the sleeve 240 in embodiments in which a sleeve 240 is present, may be fabricated as one continuous component. In other embodiments, one or more of the shaft 202 and the magnet holder 204, and the sleeve 240 in embodiments in which a sleeve 240 is present, may be fabricated as separate components that are fastened together.

Treatment of Spine with an Abnormal Curvature

The magnetic screw device of the present invention may be used to address or help treat a spine with an abnormal curvature.

Therefore, aspects of the present invention are directed to (i) a method of treating a spine with an abnormal curvature; (ii) a method of stabilizing a spine with an abnormal curvature; (iii) a method of correcting an abnormal curvature in a spine; (iv) a method of preventing curve progression of a spine with an abnormal curvature; (v) a method of reducing the risk of curve progression of a spine with an abnormal curvature; (vi) a method of aligning vertebrae in a spine with an abnormal curvature; or (vii) a method of aiding the realignment of a spine with an abnormal curvature. Aspects of the invention are also directed to the use of a magnetic screw system of the present invention to (i) treat a spine with an abnormal curvature; (ii) stabilize a spine with an abnormal curvature; (iii) correct an abnormal curvature in a spine; (iv) prevent curve progression of a spine with an abnormal curvature; (v) reduce the risk of curve progression of a spine with an abnormal curvature; (vi) align vertebrae in a spine with an abnormal curvature; or (vii) aid the realignment of a spine with an abnormal curvature. Further aspects of the invention are directed to a magnetic screw system of the present invention for use in (i) treating a spine with an abnormal curvature; (ii) stabilizing a spine with an abnormal curvature; (iii) correcting an abnormal curvature in a spine; (iv) preventing curve progression of a spine with an abnormal curvature; (v) reducing the risk of curve progression of a spine with an abnormal curvature; (vi) aligning vertebrae in a spine with an abnormal curvature; or (vii) aiding the realignment of a spine with an abnormal curvature. The magnetic screw system comprises two or more magnetic screw devices of the invention.

The methods and uses of the present invention may be applied to spinal curvatures that are at least about 10 degrees, or at least about 15 degrees, or at least about 20 degrees, or at least about 25 degrees, or at least about 30 degrees, or at least about 35 degrees, or at least about 40 degrees, or at least about 45 degrees, or at least about 50 degrees, or at least about 55 degrees, or at least about 60 degrees, or about 65 degrees, as determined using the Cobb method of measuring the degree of scoliosis. In some embodiments, the methods and uses of the present invention may be applied to spinal curvatures that are about 10 degrees to about 60 degrees, such as about 10 degrees to about 25 degrees, or about 25 degrees to about 45 degrees, or about 45 degrees to about 65 degrees, as determined using the Cobb method of measuring the degree of scoliosis.

In embodiments of the invention, these methods and uses may comprise implanting one or more of the magnetic screw devices of the present invention into each of two or more vertebrae in the area of the abnormal curvature and/or adjacent to the abnormal curvature.

The magnetic screw devices may be implanted into one pedicle of each vertebra. Alternatively, the magnetic screw devices may be implanted into both pedicles of each vertebra. The magnet screw devices may be implanted such that the stem of the magnetic screw devices is approximately perpendicular to the longitudinal axis of the spine.

The magnetic screw devices may be implanted into two or more vertebrae. In some embodiments, the magnetic screw devices may be implanted into two or more vertebrae in the area of the abnormal curvature in the spine. In some embodiments, the magnetic screw devices may be implanted into one or more vertebrae in the area of the abnormal curvature of the spine, and into one or more adjacent vertebrae. In certain embodiments, the magnetic screw devices may be implanted into two or more vertebrae, wherein at least one of the vertebrae is in the area of the abnormal curvature of the spine, and at least one of the vertebrae is not in the area of the abnormal curvature of the spine.

The magnetic screw devices may be implanted into adjacent vertebrae and, in some embodiments, in more than one adjacent vertebrae. In certain embodiments, the magnetic screw devices may be implanted into two or more vertebrae that are in the area in which the spine curves abnormally, and, in some embodiments, in the vertebrae directly adjacent to the curve(s).

In certain embodiments, the magnetic screw devices may be implanted into adjacent vertebrae that are in the area of the abnormal spinal curvature, into an adjacent vertebra immediately superior to the vertebrae in the area of the abnormal spinal curvature, and/or into an adjacent vertebra immediately inferior to the vertebrae in the area of the abnormal spinal curvature.

In certain embodiments, the magnetic screw devices may be implanted into adjacent vertebrae that are in the area of the abnormal spinal curvature, into two adjacent vertebrae immediately superior to the vertebrae in the area of the abnormal spinal curvature, and/or into two adjacent vertebrae immediately inferior to the vertebrae in the area of the abnormal spinal curvature.

In some embodiments, magnetic screw devices implanted into vertebrae may comprise a magnet holder on both ends of the shaft of the magnet assembly, may comprise a magnet holder on one end of the shaft of the magnet assembly, or there may be a combination in which one or more magnetic screw devices implanted into vertebrae may comprise a magnet holder on both ends of the shaft of the magnet assembly and one or more magnetic screw devices implanted into vertebrae may comprise a magnet holder on one end of the shaft of the magnet assembly (see, e.g., FIGS. 7 and 8). In certain embodiments, the superior-most and/or the inferior-most magnetic screw device implanted into vertebrae comprises a magnet holder on one end of the shaft of the magnet assembly.

Magnetic screw devices implanted into vertebrae may comprise magnets having the same or different magnetic strengths (e.g., due to being comprise of different magnetic materials, having a different size, etc.). In some embodiments, the magnets of the magnetic screw devices implanted into vertebrae are all of the same magnetic strength. In some embodiments, the magnets of one or more of the magnetic screw devices implanted into vertebrae have a different (greater or lesser) magnetic strength. In some embodiments in which three or more magnetic screw devices are implanted, the superior-most and/or the inferior-most magnetic screw device may comprise magnet(s) having less magnetic strength than the magnets of the other magnetic screw devices that are implanted (see, e.g., FIGS. 7 and 8).

In some embodiments, the methods and uses may be performed without manually orienting the housing of each implanted magnetic screw device. These embodiments comprise engaging the securing cap with the housing to secure the magnet assembly within the housing but without locking the housing to a particular orientation, for example, without tightening the securing cap to the housing to the extent that the housing can no longer move freely relative to the fastening stem. Such engagement allows the magnets in the magnet assembly of each magnetic screw device to self-align, resulting in the magnetic poles of the magnets in the magnet assemblies of the implanted magnetic screw devices to be in alignment.

In other embodiments, the methods and uses may comprise manually orienting the housing of one or more of the implanted magnetic screw devices so that the magnetic poles of the magnets in the magnet assembly of the magnetic screw device(s) are aligned. For each magnetic screw device, this may involve rotating and/or angling the housing relative to the fastening stem of the magnetic screw device(s) in order to orient the magnets in the magnet assembly to align their magnetic poles with the magnetic poles of magnets of other implanted magnetic screw device(s). The rotation or angle of the housing may be locked into a set orientation by further engaging (e.g., tightening) the securing cap to the extent housing to the extent that the housing can no longer move freely relative to the fastening stem.

In some embodiments, the magnetic screw devices may be implanted and/or the housing oriented such that the longitudinal axis of the magnet assembly is in a particular orientation relative to the spine or the curvature. In some embodiments, magnetic screw devices may be implanted such that the longitudinal axis of the magnet assembly may be parallel or approximately parallel with the longitudinal axis of the spine. In some embodiments, magnetic screw devices may be implanted such that the longitudinal axis of the magnet assembly may be angled relative to the longitudinal axis of the spine, for an example an angle of about 5 degrees to about 60 degrees, such as about 10 degrees to about 25 degrees, or about 25 degrees to about 45 degrees, or about 45 degrees to about 65 degrees, including, for instance, an angle of about 5 degrees, or about 10 degrees, or about 15 degrees, or about 20 degrees, or about 25 degrees, or about 30 degrees, or about 35 degrees, or about 40 degrees, or about 45 degrees, or about 50 degrees, or about 55 degrees, or about 60 degrees, or about 65 degrees. In some embodiments, magnetic screw devices may be implanted such that the longitudinal axis of the magnet assembly is at the same angle as the curvature.

The centering force (i.e., the force compelling the vertebrae to align) that is generated from the presence of the magnets is affected by the number of magnets implanted, the magnet offset (angle of curvature) present in the spine, as well as the strength of the individual magnets, which is controlled in part by the shape and size of the magnets. But the magnetic force field generated by the magnetic poles of each of the magnets being in the same direction can result in an attempted vertical alignment of the magnets, and consequently an attempted vertical alignment or stacking of the vertebral bodies into which the magnetic devices are implanted.

In some embodiments, the placement of the magnetic screw devices and the orientation of their housing assemblies relative to each other may be predetermined based on imaging (such as radiographic imaging) of the spine and measurements of the deformity (such as degrees of scoliosis using the Cobb method).

In certain embodiments, to treat an abnormal curvature of the spine, e.g., C-type curve, S-type curve, or double S-type curve, magnetic screw devices may be implanted in one pedicle or both pedicles of two or more vertebrae, or each vertebra, in the area of the curve. In some embodiments, magnetic screw devices may be implanted in the vertebra at the base of the area of the abnormal curve (e.g., most inferior vertebra in the area of the abnormal curve) only or in the vertebra at the top of the area of the abnormal curve (e.g., most superior vertebra in the area of the abnormal curve) only; in each vertebra in the area of the abnormal curve; in each vertebra in the area of the abnormal curve and in one vertebra superior and/or inferior to the area of the abnormal curve; or in each vertebra in the area of the abnormal curve and in more than one vertebra superior and/or inferior to the area of the abnormal C-type curve.

In some embodiments, implantation of magnetic screw devices superior and inferior to the area of the abnormal spinal curve may help mitigate the vertical load (loading in the direction of the mid-line axis of the spine) on the vertebrae in the area of the abnormal spinal curve and, in some embodiments, on the vertebrae superior and/or inferior to the area of the abnormal spinal curve. To this end, embodiments of the present invention relate to a method of mitigating vertical load in vertebrae of a spine undergoing treatment for an abnormal spinal curvature, the method comprising implanting magnetic screw devices according to embodiments of the invention as described herein.

In embodiments of the present invention, an external brace may be used in conjunction with the magnetic screw devices. The external brace may provide an attractive straightening force to stabilize the spine and prevent further progression of the abnormal curvature. The external brace may comprise one or more magnets, which can be larger than the magnets used in the magnetic screw devices. With the use of the external brace, magnetic screw devices do not have to be implanted in both pedicles of a vertebra or in each of the vertebrae that are located in the area of the abnormal curvature or adjacent thereto. In other embodiments, the external brace may not have any magnets and may be used to provide additional support to the spine.

In some embodiments, the combination of implanting one or more magnetic screw devices and having the subject wear an external brace may be used to provide more complex straightening loading in highly distorted abnormal three-dimensionally curved spines, because greater diversity in placement can be utilized internally and externally in the brace.

Kits

An aspect of the invention relates to kits that comprise:
(a) two or more constructs comprising a fastening stem assembled with a housing ("fastening stem-housing construct");
(b) two or more magnet assemblies;
(c) two or more magnets; and
(d) instructions on how to assemble magnetic screw devices from the fastening stem-housing constructs securing caps, magnet assemblies, and magnets, and/or how to implant the magnetic screw devices.

In some embodiments, the kit comprises more than one set of magnet assemblies, in which each set comprises at least two magnet assemblies, and each set differs from each other by the length of the shaft of the magnet assembly, size of the bore of the magnet holder, shape of the bore of the magnet holder, or a combination thereof. In such embodiments, the kit includes a set of magnets that can fit within the magnet holders of each set of magnet assemblies.

In some embodiments, the kit comprises more than one set of magnets, in which each set comprises at least two magnets, and each set differs from each other by the polarity of the magnet, size of the magnet, shape of the magnet, or a combination thereof. In such embodiments, the kit includes a set of magnet assemblies comprising a magnet holder that can accommodate each set of magnets.

The instructions on how to assemble magnetic screw devices from the fastening stem-housing constructs, securing caps, magnet assemblies, and magnets may comprise steps placing a magnet into the bore of each magnet holder, enclosing the magnet within the bore using the cap of the magnet assembly, and securing the magnet assembly to the housing using the securing cap.

EXAMPLES

The following example used modeling to assess the centering (horizontal) forces and vertical forces generated by implanted magnetic screw devices for different types of abnormal spinal curvatures.

The horizontal and vertical forces were modeled using JMAG simulation technology. JMAG utilizes finite element analysis to calculate the magnetic forces and fields. Briefly, the geometry of the magnets was loaded into the simulation software, and the magnetic material properties (N52 grade NdFeB) and pole orientation were assigned when the simulation was performed.

For the horizontal forces calculated in the analysis, a positive value represents a force pushing the vertebra to the right, and a negative value represents a force pushing the vertebra to the left. For the vertical forces, a positive value represents a force pushing the vertebra in the superior direction, i.e., cranially, and a negative value represents a force pushing the vertebra in the inferior direction, i.e., caudally.

Example 1

Figure 5:
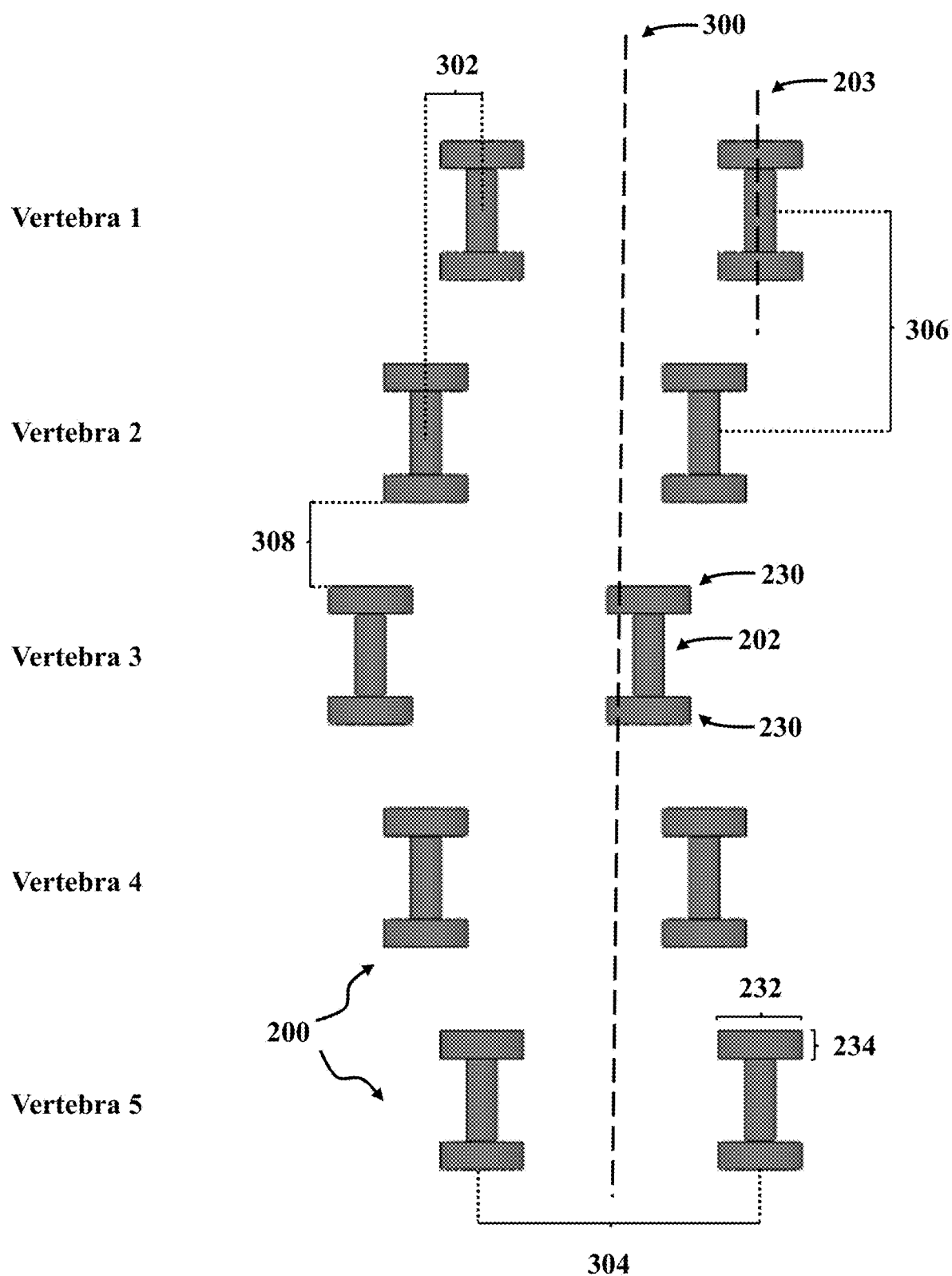
FIG. 5 shows a configuration of implanted magnetic screw devices (with only the magnet assemblies shown) relative to a 5-vertebrae-level abnormal C-type spinal curvature, in which the longitudinal axis of the magnet assemblies is parallel to the longitudinal axis of the spine, according to embodiments of the present invention.

An analysis was performed to calculate the horizontal and vertical forces generated by magnetic screw devices according to the present invention, implanted in both pedicles of five adjacent vertebrae (numbered Vertebrae 1-5, in which Vertebra 1 is the superior-most vertebra, Vertebra 5 is the inferior-most vertebra, and Vertebra 3 is the middle vertebra) in the area of an abnormal C-type spinal curvature having a horizontal offset distance 302 (i.e., horizontal distance between the corresponding pedicles of adjacent vertebrae) of 10 mm (14°), in which the magnetic screw devices were oriented such that the longitudinal axis 203 of the magnet assembly 200 of the magnetic screw devices was parallel to the longitudinal axis 300 of the spine, as depicted in FIG. 5.

The analysis considered implantation of the magnetic screw devices at a horizontal separation 304 (i.e., distance between the magnetic screw devices in the left and right pedicles of the same vertebra) of 50 mm, and a vertical separation 306 (i.e., distance between the magnetic screw devices in corresponding pedicles of adjacent vertebrae) of 40 mm. Each magnetic screw device comprised a magnet 230 (in a magnet holder) on each end of the shaft 202 of the magnet assembly 200, in which each magnet 230 comprised a diameter 232 of 15 mm and a length 234 of 5 mm or 7.5 mm. All magnets 230 were oriented with their north poles in the same direction in order to generate attractive forces. The length of the shaft 202 of the magnet assembly 200 was 15 mm or 20 mm. The magnet separation distance 308 (i.e., distance between the magnets 230 of the magnetic screw devices implanted in corresponding pedicles of adjacent vertebrae) was 15 mm, 10 mm, or 5 mm.

The results of the analysis are presented in Tables 1 and 2, which show the horizontal forces and vertical forces, respectively, generated by the magnetic screw devices. The forces generated by both magnetic screw devices in each vertebra were summed to calculate the net force on each body. As shown in Table 1, the greatest horizontal force was generated at Vertebra 3, but horizontal forces were also generated at Vertebrae 1 and 5. The horizontal force at Vertebra 3 was nearly twice in magnitude as compared to the horizontal forces at Vertebrae 1 and 5. Further, in general, greater horizontal forces were generated when the magnet length was greater, when the shaft length was greater, and when the magnet separation distance was smaller.

TABLE 1

Horizontal forces generated by magnetic screw devices
implanted in both pedicles of adjacent vertebrae in the
area of a 5-level abnormal C-curve, in which the
longitudinal axis of the magnet assembly of the magnetic
screw devices was parallel to the longitudinal axis of
the spine.

| | Horizontal Force (N) Magnet Length (mm) | | | |
|---|---|---|---|---|
| | 5 | 5 | 7.5 | 7.5 |
| | Shaft Length (mm) | | | |
| | 15 | 20 | 15 | 20 |
| | Magnet Separation Distance (mm) | | | |
| | 15 | 10 | 10 | 5 |
| Vertebra 1 (superior-most of the curve) | −2.80 | −6.25 | −10.91 | −24.31 |
| Vertebra 2 | −0.04 | 0.09 | −0.70 | 0.02 |
| Vertebra 3 (middle of the curve) | 5.49 | 12.11 | 20.73 | 47.07 |
| Vertebra 4 | 0.08 | 0.20 | 0.18 | 0.84 |
| Vertebra 5 (inferior-most of the curve) | −2.68 | −6.13 | −10.98 | −24.09 |

As shown in Table 2, the greatest vertical force was generated at Vertebrae 1 and 5. There was not a substantial difference in the vertical forces generated at Vertebrae 2, 3, and 4. In general, greater vertical forces were generated when the magnet length was greater, when the shaft length was greater, and when the magnet separation distance was smaller.

TABLE 2

Vertical forces generated by magnetic screw devices
implanted in both pedicles of adjacent vertebrae in the area
of a 5-level abnormal C-curve, in which the longitudinal axis
of the magnet assembly of the magnetic screw devices
was parallel to the longitudinal axis of the spine.

| | Vertical Force (N) Magnet Length (mm) | | | |
|---|---|---|---|---|
| | 5 | 5 | 7.5 | 7.5 |
| | Shaft Length (mm) | | | |
| | 15 | 20 | 15 | 20 |
| | Magnet Separation Distance (mm) | | | |
| | 15 | 10 | 10 | 5 |
| Vertebra 1 (superior-most of the curve) | −2.68 | −4.06 | −8.62 | −10.66 |
| Vertebra 2 | −0.04 | −0.13 | −1.35 | −0.33 |
| Vertebra 3 (middle of the curve) | 0.11 | 0.04 | −0.85 | 0.32 |
| Vertebra 4 | 0.45 | 0.12 | 0.62 | −0.04 |
| Vertebra 5 (inferior-most of the curve) | 2.67 | 4.03 | 9.18 | 10.59 |

Example 2

Figure 6:
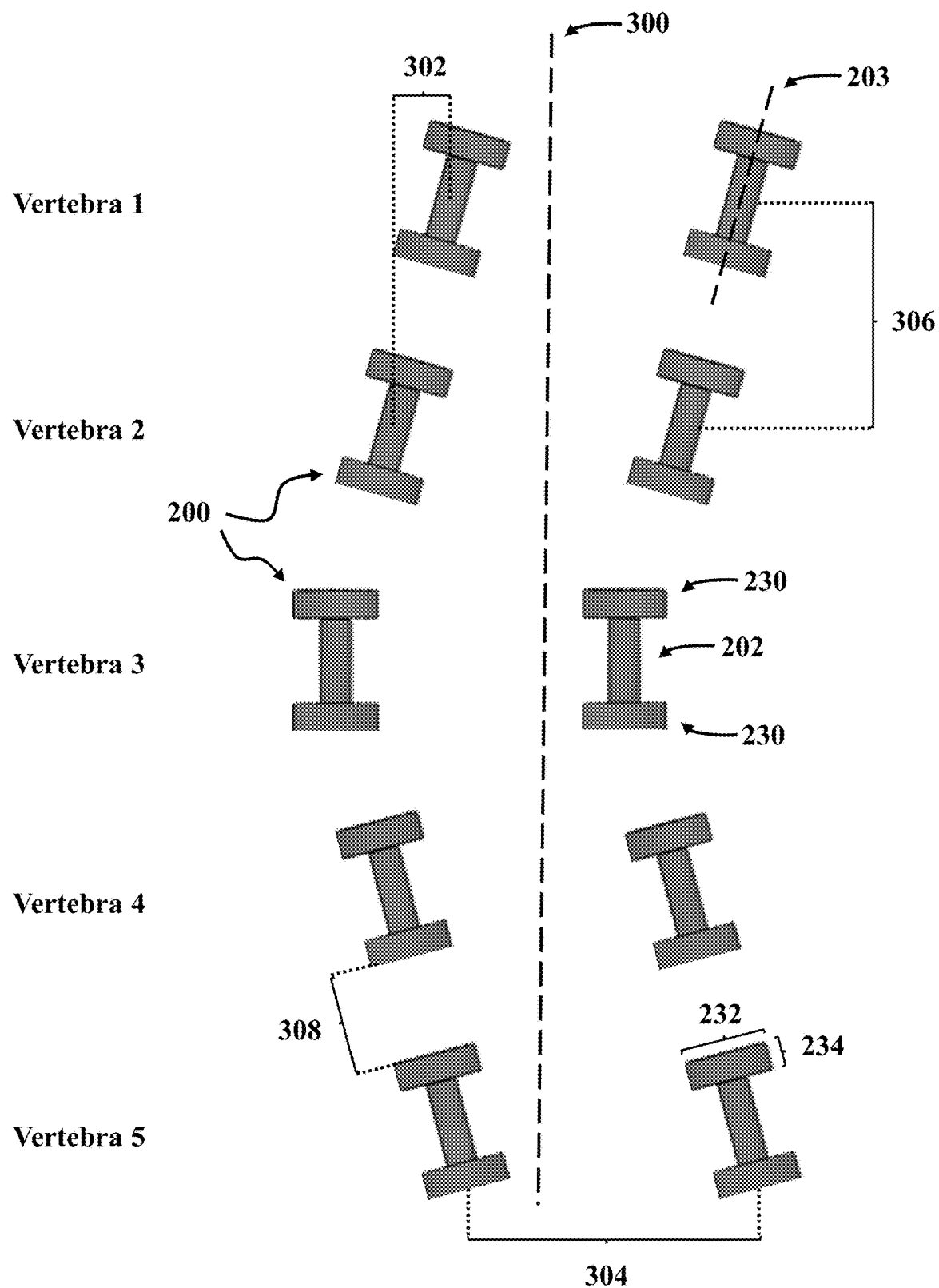
FIG. 6 shows a configuration of implanted magnetic screw devices (with only the magnet assemblies shown) relative to a 5-vertebrae-level abnormal C-type spinal curvature, in which the longitudinal axis of the magnet assemblies is angled relative to the longitudinal axis of the spine, according to embodiments of the present invention.

An analysis was performed to calculate the horizontal and vertical forces generated by magnetic screw devices according to the present invention, implanted in both pedicles of five adjacent vertebrae (numbered Vertebrae 1-5, in which Vertebra 1 is the superior-most vertebra, Vertebra 5 is the inferior-most vertebra, and Vertebra 3 is the middle vertebra) in the area of an abnormal C-type spinal curvature having a horizontal offset distance 302 of 10 mm (14°), in which the magnetic screw devices were oriented such that the longitudinal axis 203 of the magnet assembly 200 of the magnetic screw devices was angled to match the curvature of the spine, as shown in FIG. 6.

The analysis considered implantation of the magnetic screw devices at a horizontal separation 304 of 50 mm, and a vertical separation 306 of 40 mm. Each magnetic screw device comprised a magnet 230 (in a magnet holder) on each end of the shaft 202 of the magnet assembly 200, in which each magnet 230 comprised a diameter 232 of 15 mm and a length 234 of 5 mm or 7.5 mm. All magnets 230 were oriented with their north poles in the same direction in order to generate attractive forces. The length of the shaft 202 of the magnet assembly 200 was 15 mm or 20 mm. The magnet separation distance 308 was 15 mm, 10 mm, or 5 mm.

The results of the analysis are presented in Tables 3 and 4, which show horizontal forces and vertical forces, respectively, generated by the magnetic screw devices. The forces generated by both magnetic screw devices in each vertebra were summed to calculate the net force on each body. As shown in Table 3, the greatest horizontal force was generated at Vertebra 3, but horizontal forces were also generated at Vertebrae 1 and 5. The horizontal force at Vertebra 3 was nearly three times in magnitude as compared to the horizontal forces at Vertebrae 1 and 5. Also, in general, greater horizontal forces were generated when the magnet length was greater, when the shaft length was greater, and when the magnet separation distance was smaller.

Compared to Example 1, in which the magnetic screw devices were not implanted at the same angle as the spinal curvature, the horizontal forces in Example 2 were similarly greatest at Vertebra 3, but there was a greater difference in the horizontal forces generated in Vertebra 3 versus Vertebrae 1 and 5. Further, for each magnet length, each shaft length, and each magnet separation distance, the absolute horizontal force was greater at Vertebrae 2 and 4, and less at Vertebra 1 and 5, when the magnetic screw devices were implanted at the orientation of Example 2 as compared to the orientation of Example 1.

TABLE 3

Horizontal forces generated by magnetic screw devices
implanted in both pedicles of adjacent vertebrae in the
area of a 5-level abnormal C-curve, in which the magnetic
screw devices were oriented such that the longitudinal
axis of the magnet assembly of the magnetic screw devices
was angled to match the curvature of the spine.

| | Horizontal Force (N) Magnet Length (mm) | | | |
|---|---|---|---|---|
| | 5 | 5 | 7.5 | 7.5 |
| | Shaft Length (mm) | | | |
| | 15 | 20 | 15 | 20 |
| | Magnet Separation Distance (mm) | | | |
| | 15 | 10 | 10 | 5 |
| Vertebra 1 (superior-most of the curve) | −1.19 | −2.22 | −5.37 | −12.80 |
| Vertebra 2 | −0.91 | −2.73 | −3.40 | −13.80 |
| Vertebra 3 (middle of the curve) | 4.26 | 11.68 | 19.19 | 51.06 |
| Vertebra 4 | −0.97 | −2.83 | −5.07 | −12.33 |
| Vertebra 5 (inferior-most of the curve) | −1.29 | −2.74 | −5.06 | −13.51 |

As shown in Table 4, the greatest vertical force was generated at Vertebrae 1 and 5. There were also smaller vertical forces generated at Vertebrae 2 and 4. Generally, greater vertical forces were generated when the magnet length was greater, when the shaft length was greater, and when the magnet separation distance was smaller.

Compared to Example 1, in which the magnetic screw devices were not implanted at the same angle as the spinal curvature, the vertical forces shown in Example 2 were similarly greatest at Vertebra 1 and 5, but the magnitude of the vertical forces was 2-4 times larger. Further, for each magnet length, each shaft length, and each magnet separation distance, the absolute vertical force was greater at Vertebrae 2 and 4 when the magnetic screw devices were implanted at the orientation of Example 2 as compared to the orientation of Example 1.

TABLE 4

Vertical forces generated by magnetic screw devices implanted in both pedicles of adjacent vertebrae in the area of a 5-level abnormal C-curve, in which the magnetic screw devices were oriented such that the longitudinal axis of the magnet assembly of the magnetic screw devices was angled to match the curvature of the spine.

| | Vertical Force (N) Magnet Length (mm) | | | |
|---|---|---|---|---|
| | 5 | 5 | 7.5 | 7.5 |
| | Shaft Length (mm) | | | |
| | 15 | 20 | 15 | 20 |
| | Magnet Separation Distance (mm) | | | |
| | 15 | 10 | 10 | 5 |
| Vertebra 1 (superior-most of the curve) | −4.60 | −9.51 | −19.93 | −44.99 |
| Vertebra 2 | 0.41 | 1.34 | 6.71 | 16.01 |
| Vertebra 3 (middle of the curve) | −0.12 | 0.00 | −2.63 | 0.13 |
| Vertebra 4 | −0.62 | −1.93 | −4.78 | −16.34 |
| Vertebra 5 (inferior-most of the curve) | 4.64 | 10.00 | 19.78 | 45.08 |

Example 3

An analysis was performed to calculate the horizontal and vertical forces generated by magnetic screw devices according to the present invention, implanted in both pedicles of five adjacent vertebrae (numbered Vertebrae 1-5, in which Vertebra 1 is the superior-most vertebra, Vertebra 5 is the inferior-most vertebra, and Vertebra 3 is the middle vertebra) in the area of an abnormal C-type spinal curvature having a horizontal offset distance 302 of 10 mm (14°), in which the magnetic screw devices were oriented such that the longitudinal axis 203 of the magnet assembly 200 of the magnetic screw devices was parallel to the longitudinal axis 300 of the spine, as depicted in FIG. 7. Magnetic screw devices were also implanted in both pedicles of an adjacent vertebra superior to the area of the curvature (Vertebra A) and an adjacent vertebra inferior to the area of the curvature (Vertebra B), as shown in FIG. 7.

The analysis considered implantation of the magnetic screw devices at a horizontal separation 304 of 50 mm, and a vertical separation 306 of 40 mm. Each magnetic screw device implanted in vertebrae in the area of the curvature comprised a magnet 230 (in a magnet holder) on each end of the shaft 202 of the magnet assembly 200, in which each magnet 230 comprised a diameter 232 of 15 mm and a length 234 of 5 mm or 7.5 mm. Each magnetic screw device implanted in vertebrae adjacent to the area of the curvature comprised a magnet 230 (in a magnet holder) on one end of the shaft 202 of the magnet assembly 200, in which the magnet 230 comprised a diameter 232 of 10.6 mm and a length 234 of 5 mm or 7.5 mm. All magnets 230 were oriented with their north poles in the same direction in order to generate attractive forces. The length of the shaft 202 of the magnet assembly 200 was 15 mm or 20 mm. The magnet separation distance 308 was 15 mm, 10 mm, or 5 mm.

The results of the analysis are presented in Tables 5 and 6, which show the horizontal forces and vertical forces, respectively, generated by the magnetic screw devices. The forces generated by both magnetic screw devices in each vertebra were summed to calculate the net force on each body. As shown in Table 5, the greatest horizontal force was generated at Vertebra 3, but horizontal forces were also generated at Vertebrae 1 and 5. The horizontal force at Vertebra 3 was nearly twice in magnitude as compared to the horizontal forces at Vertebrae 1 and 5. Further, in general, greater horizontal forces were generated when the magnet length was greater, when the shaft length was greater, and when the magnet separation distance was smaller.

Compared to Example 1, in which magnetic screw devices were implanted only in the area of the C-curve, the horizontal forces resulting in Example 3 were also greatest at the middle vertebra of the C-curve. Further, for each magnet length, each shaft length, and each magnet separation distance, the horizontal force at each vertebra of the curvature were similar.

TABLE 5

Horizontal forces generated by magnetic screw devices implanted in both pedicles of adjacent vertebrae in the area of a 5-level abnormal C-curve, and in both pedicles of an adjacent vertebra superior to the area of the abnormal C-curve and an adjacent vertebra inferior to the area of the abnormal C-curve, in which the longitudinal axis of the magnet assembly of the magnetic screw devices was parallel to the longitudinal axis of the spine.

| | Horizontal Force (N) Magnet Length (mm) | | | |
|---|---|---|---|---|
| | 5 | 5 | 7.5 | 7.5 |
| | Shaft Length (mm) | | | |
| | 15 | 20 | 15 | 20 |
| | Magnet Separation Distance (mm) | | | |
| | 15 | 10 | 10 | 5 |
| Vertebra A (adjacent to the curve) | −0.03 | 0.01 | −0.04 | −0.01 |
| Vertebra 1 (superior-most of the curve) | −2.77 | −6.00 | −11.03 | −23.46 |
| Vertebra 2 | −0.04 | −0.07 | 0.27 | 0.22 |
| Vertebra 3 (middle of the curve) | 5.33 | 12.20 | 21.00 | 47.83 |
| Vertebra 4 | 0.02 | −0.16 | 0.25 | 0.72 |
| Vertebra 5 (inferior-most of the curve) | −2.82 | −6.27 | −10.23 | −24.15 |
| Vertebra B (adjacent to the curve) | −0.11 | −0.04 | −0.13 | 0.16 |

As shown in Table 6, the greatest vertical force was generated at the vertebrae adjacent to the area of the C-curve (Vertebrae A and B). There was not a substantial difference in the vertical forces generated at Vertebrae 2, 3, and 4. In general, greater vertical forces were generated when the magnet length was greater, when the shaft length was greater, and when the magnet separation distance was smaller.

Compared to Example 1, in which magnetic screw devices were implanted only at the area of the C-curve, the vertical forces resulting in Example 3 were also greatest at the outermost vertebrae in which the magnetic screw devices were implanted. i.e., at Vertebrae A and B of Example 3 and at Vertebrae 1 and 5 of Example 1. However, the magnitude of the vertical force was greater at each outermost vertebra in Example 1 except for when the magnet length was 7.5 mm and the shaft length was 15 mm.

TABLE 6

Vertical forces generated by magnetic screw devices implanted in both pedicles of adjacent vertebrae in the area of a 5-level abnormal C-curve, and in both pedicles of an adjacent vertebra superior to the area of the abnormal C-curve and an adjacent vertebra inferior to the area of the abnormal C-curve, in which the longitudinal axis of the magnet assembly of the magnetic screw devices was parallel to the longitudinal axis of the spine.

| | Vertical Force (N) Magnet Length (mm) | | | |
|---|---|---|---|---|
| | 5 | 5 | 7.5 | 7.5 |
| | Shaft Length (mm) | | | |
| | 15 | 20 | 15 | 20 |
| | Magnet Separation Distance (mm) | | | |
| | 15 | 10 | 10 | 5 |
| Vertebra A (adjacent to the curve) | −2.69 | −6.64 | −5.01 | −17.91 |
| Vertebra 1 (superior-most of the curve) | 0.16 | 2.64 | −3.89 | 5.13 |
| Vertebra 2 | −0.12 | −0.31 | −0.13 | −0.12 |
| Vertebra 3 (middle of the curve) | −0.02 | −0.13 | −0.01 | 0.42 |
| Vertebra 4 | 0.21 | 0.23 | 1.25 | −0.08 |
| Vertebra 5 (inferior-most of the curve) | −0.27 | −2.33 | 3.99 | −4.63 |
| Vertebra B (adjacent to the curve) | 2.76 | 6.15 | 5.13 | 17.16 |

Example 4

An analysis was performed to calculate the horizontal and vertical forces generated by magnetic screw devices according to the present invention, implanted in both pedicles of five adjacent vertebrae (numbered Vertebrae 1-5, in which Vertebra 1 is the superior-most vertebra, Vertebra 5 is the inferior-most vertebra, and Vertebra 3 is the middle vertebra) in the area of an abnormal C-type spinal curvature having a horizontal offset distance 302 of 10 mm (14°), in which the magnetic screw devices were oriented such that the longitudinal axis 203 of the magnet assembly 200 of the magnetic screw devices was angled to match the curvature of the spine, as shown in FIG. 8. Magnetic screw devices were also implanted in both pedicles of an adjacent vertebra superior to the area of the curvature (Vertebra A) and an adjacent vertebra inferior to the area of the curvature (Vertebra B), as shown in FIG. 8.

The analysis considered implantation of the magnetic screw devices at a horizontal separation 304 of 50 mm, and a vertical separation 306 of 40 mm. Each magnetic screw device implanted in vertebrae in the area of the curvature comprised a magnet 230 (in a magnet holder) on each end of the shaft 202 of the magnet assembly 200, in which each magnet 230 comprised a diameter 232 of 15 mm and a length 234 of 5 mm or 7.5 mm. Each magnetic screw device implanted in vertebrae adjacent to the area of the curvature comprised a magnet 230 (in a magnet holder) on one end of the shaft 202 of the magnet assembly 200, in which the magnet 230 comprised a diameter 232 of 10.6 mm and a length 234 of 5 mm or 7.5 mm. All magnets 230 were oriented with their north poles in the same direction in order to generate attractive forces. The length of the shaft 202 of the magnet assembly 200 was 15 mm or 20 mm. The magnet separation distance 308 was 15 mm, 10 mm, or 5 mm.

The results of the analysis are presented in Tables 7 and 8, which show the horizontal forces and vertical forces, respectively, generated by the magnetic screw devices. The forces generated by both magnetic screw devices in each vertebra were summed to calculate the net force on each body. As shown in Table 7, the greatest horizontal force was generated at Vertebra 3, but horizontal forces were also generated at Vertebrae 1 and 5. The horizontal force at Vertebra 3 was nearly 2.5 times in magnitude as compared to the horizontal forces at Vertebrae 1 and 5. Further, in general, greater horizontal forces were generated when the magnet length was greater, when the shaft length was greater, and when the magnet separation distance was smaller.

Compared to Example 2, in which magnetic screw devices were implanted only at the area of the C-curve, the horizontal forces resulting in Example 4 were also greatest at the middle vertebra of the C-curve. Further, at each vertebra, for each magnet length, each shaft length, and each magnet separation distance, the horizontal force at each vertebra of the curvature were similar.

Compared to Example 3, in which the magnetic screw devices were not implanted at the same angle as the spinal curvature, the horizontal forces shown in Example 4 were similarly greatest at Vertebra 3, but there was a smaller difference in the horizontal forces generated in Vertebra 3 versus Vertebrae 1 and 5. Further, for each magnet length, each shaft length, and each magnet separation distance, the absolute horizontal force was greater at the vertebrae adjacent to the area of the curvature and at Vertebrae 2 and 4 when the magnetic screw devices were implanted at the orientation of Example 4 as compared to the orientation of Example 3; however, the absolute horizontal force was less at the superior- and inferior-most vertebrae in the area of the curvature when the magnetic screw devices were implanted at the orientation of Example 4 as compared to the orientation of Example 3.

TABLE 7

Horizontal forces generated by magnetic screw devices implanted in both pedicles of adjacent vertebrae in the area of a 5-level abnormal C-curve, and in both pedicles of an adjacent vertebra superior to the area of the abnormal C-curve and an adjacent vertebra inferior to the area of the abnormal C-curve, in which the magnetic screw devices were oriented such that the longitudinal axis of the magnet assembly of the magnetic screw devices was angled to match the curvature of the spine.

| | Horizontal Force (N) Magnet Length (mm) | | | |
|---|---|---|---|---|
| | 5 | 5 | 7.5 | 7.5 |
| | Shaft Length (mm) | | | |
| | 15 | 20 | 15 | 20 |
| | Magnet Separation Distance (mm) | | | |
| | 15 | 10 | 10 | 5 |
| Vertebra A (adjacent to the curve) | 0.83 | 2.27 | 1.57 | 7.13 |
| Vertebra 1 (superior-most of the curve) | −2.06 | −4.84 | −7.11 | −19.06 |
| Vertebra 2 | −0.79 | −2.56 | −4.21 | −11.75 |
| Vertebra 3 (middle of the curve) | 4.46 | 11.68 | 19.63 | 50.49 |
| Vertebra 4 | −0.97 | −2.96 | −4.03 | −11.78 |
| Vertebra 5 (inferior-most of the curve) | −2.03 | −4.89 | −6.24 | −19.47 |
| Vertebra B (adjacent to the curve) | 0.79 | 2.36 | 1.64 | 7.02 |

As shown in Table 8, the greatest vertical force was generated at the vertebrae adjacent to the area of the C-curve (Vertebrae A and B). In general, greater vertical forces were generated when the magnet length was greater, when the shaft length was greater, and when the magnet separation distance was smaller.

Compared to Example 2, in which magnetic screw devices were implanted only at the area of the C-curve, the horizontal forces resulting in Example 4 were also greatest at the outermost vertebrae in which magnetic screw devices were implanted. i.e., at Vertebrae A and B of Example 4 and at Vertebrae 1 and 5 of Example 2. However, the magnitude of the vertical forces at the outermost vertebrae in Example 4 were about 30-70%. less than the magnitude of the vertical forces at the outermost vertebrae in Example 2.

Compared to Example 3, in which the magnetic screw devices were not implanted at the same angle as the spinal curvature, the vertical forces shown in Example 3 were similarly greatest at the superior-most and inferior-most vertebrae in the area of the curvature, i.e., Vertebra 1 and 5, but the magnitude of the vertical forces was generally smaller. Further, for each magnet length, each shaft length, and each magnet separation distance, the absolute vertical force was greater at Vertebrae 2 and 4 when the magnetic screw devices were implanted at the orientation of Example 4 as compared to the orientation of Example 3.

TABLE 8

Vertical forces generated by magnetic screw devices implanted in both pedicles of adjacent vertebrae in the area of a 5-level abnormal C-curve, and in both pedicles of an adjacent vertebra superior to the area of the abnormal C-curve and an adjacent vertebra inferior to the area of the abnormal C-curve, in which the magnetic screw devices were oriented such that the longitudinal axis of the magnet assembly of the magnetic screw devices was angled to match the curvature of the spine.

| | Vertical Force (N) Magnet Length (mm) | | | |
|---|---|---|---|---|
| | 5 | 5 | 7.5 | 7.5 |
| | Shaft Length (mm) | | | |
| | 15 | 20 | 15 | 20 |
| | Magnet Separation Distance (mm) | | | |
| | 15 | 10 | 10 | 5 |
| Vertebra A (adjacent to the curve) | −2.38 | −5.87 | −4.30 | −15.16 |
| Vertebra 1 (superior-most of the curve) | −2.32 | −3.92 | −13.73 | −32.08 |
| Vertebra 2 | 0.51 | 1.99 | 4.20 | 15.69 |
| Vertebra 3 (middle of the curve) | 0.08 | −0.10 | −0.55 | −0.27 |
| Vertebra 4 | −0.83 | −2.06 | −4.80 | −16.26 |
| Vertebra 5 (inferior-most of the curve) | 2.29 | 3.86 | 13.84 | 32.48 |
| Vertebra B (adjacent to the curve) | 2.36 | 5.80 | 4.40 | 14.77 |

The horizontal forces generated by the magnetic screw devices demonstrated in these Examples are similar to the forces generated by existing implant screw and rod systems. (See, e.g., Abe et al. 2015; Lou et al. 2002; Salmingo et al. 2012; Salmingo et al. 2013). These results indicate that the magnetic screw devices of the present invention are capable of generating corrective forces that can treat abnormal spine curvatures.

REFERENCES

Abe Y, et al. Scoliosis corrective force estimation from the implanted rod deformation using 3D-FEM analysis. *Scoliosis*. 10: 1-6 (2015).
Lou E, el al. Instrumented rod rotator system for spinal surgery. *Med. Biol. Eng. Comput.* 40: 376-379 (2002).
Salmingo R, et al. Corrective force analysis for scoliosis from implant rod deformation. *Clin. Biomech.* 27: 545-550 (2012).
Salmingo R A, et al. Relationship of forces acting on implant rods and degree of scoliosis correction. *Clin. Biomech.* 28: 122-128 (2013).

What is claimed is:

1. A magnetic screw device comprising a fastening stem, a housing, a magnet assembly, and one or more magnets, wherein
   the fastening stem comprises a first end, a second end, a shank therebetween, and a longitudinal axis therebetween, wherein the first end comprises a spherical or part spherical surface, the second end comprises a taper to a pointed or approximately pointed shape, and the shank comprises a thread;
   the housing comprises a top end, a bottom end, wall therebetween, and a bore between the top end and bottom end that defines an inner surface, wherein a portion of the inner surface adjacent to the bottom end comprises a concave spherical or part-spherical surface that is configured to engage with the spherical or part-spherical surface of the first end of the fastening stem; and wherein the housing comprises a first slot and a second slot that extends from the top end towards the bottom end and is located on opposing sites of the wall;

the magnet assembly comprises a shaft, a magnet holder on one or both ends of the shaft, a removable holder cap for each magnet holder, a longitudinal axis extending between the ends of the shaft, and a sleeve adjacent to each end of the shaft, wherein each magnet holder comprises an outer surface, a bore defining an inner surface, a closed end, and an open end; wherein each holder cap is configured to enclose the open end of the magnet holder; wherein the shaft is removably received by the first slot and second slot of the housing; and wherein the shaft is configured to extend between the first slot and the second slot of the housing; and each magnet is configured to be received by one of the magnet holders.

2. The magnetic screw device of claim 1, wherein the first end of the fastening stem comprises a drive on its surface, wherein the drive is configured to receive a driver.

3. The magnetic screw device of claim 1, wherein the engagement of the portion of the inner surface having a concave spherical or part-spherical surface with the spherical or part-spherical surface of the first end of the fastening stem permits the housing to rotate up to 360 degrees.

4. The magnetic screw device of claim 1, wherein the engagement of the portion of the inner surface having a concave spherical or part-spherical surface with the spherical or part-spherical surface of the first end of the fastening stem permits the housing to tilt in the range of about 50 to about 100 degrees relative to the longitudinal axis of the fastening stem.

5. The magnetic screw device of claim 1, wherein if the end of the shaft comprises a magnet holder, the sleeve is between the magnet holder and the shaft.

6. The magnetic screw device of claim 5, wherein each sleeve is positioned such that it is adjacent to one of the first slot or the second slot when the shaft is received by the first slot and second slot.

7. The magnetic screw device of claim 1, wherein the housing further comprises a securing cap that is configured to engage with the housing at its top end via a locking mechanism.

8. The magnetic screw device of claim 7, wherein the engagement of the securing cap with the housing secures the magnet assembly within the housing.

9. The magnetic screw device of claim 7, wherein the engagement of the securing cap with the housing secures the magnet assembly within the housing and prevents rotational and angular movement of the housing relative to the fastening stem.

10. The magnetic screw device of claim 1, wherein the magnets in each of the magnet holders have the same polarity.

11. A magnetic screw system comprising two or more magnetic screw devices according to claim 1.

12. A method of treating a spine with an abnormal curvature in a subject in need thereof, the method comprising implanting one or more magnetic screw devices into each of two or more vertebrae at the curvature, adjacent to the curvature, or a combination thereof, wherein each magnetic screw device comprises a fastening stem, a housing, a magnet assembly, and one or more magnets, wherein the fastening stem comprises a first end, a second end, a shank therebetween, and a longitudinal axis therebetween, wherein the first end comprises a spherical or part spherical surface, the second end comprises a taper to a pointed or approximately pointed shape, and the shank comprises a thread;

the housing comprises a top end, a bottom end, wall therebetween, and a bore between the top end and bottom end that defines an inner surface, wherein a portion of the inner surface adjacent to the bottom end comprises a concave spherical or part-spherical surface that is configured to engage with the spherical or part-spherical surface of the first end of the fastening stem; and wherein the housing comprises a first slot and a second slot that extends from the top end towards the bottom end and is located on opposing sites of the wall;

the magnet assembly comprises a shaft, a magnet holder on one or both ends of the shaft, a removable holder cap for each magnet holder, a longitudinal axis extending between the ends of the shaft, and a sleeve adjacent to each end of the shaft, wherein e ach magnet holder comprises an outer surface, a bore defining an inner surface, a closed end, and an open end; wherein each holder cap is configured to enclose the open end of the magnet holder; wherein the shaft is removably received by the first slot and second slot of the housing; and wherein the shaft is configured to extend between the first slot and the second slot of the housing;

and each magnet is configured to be received by one of the magnet holders.

13. The method of claim 12, comprising implanting the magnetic screw device into one of the pedicles of each of two or more vertebrae.

14. The method of claim 12, comprising implanting the magnetic screw device into both pedicles of each of two or more vertebrae.

15. The method of claim 12, comprising orienting the housing such that the longitudinal axis of the magnet assembly is approximately parallel with the longitudinal axis of the spine.

16. The method of claim 12, comprising orienting the housing such that the longitudinal axis of the magnet assembly is angled relative to the longitudinal axis of the spine.

17. The method of claim 12, wherein the magnet on each magnetic screw device is oriented to have the same magnetic pole alignment.

18. The method of claim 12, further comprising implanting one or more magnetic screw devices into two or more vertebrae that are adjacent to the vertebrae at the curvature.

19. A method of preventing curve progression of a spine with an abnormal curvature in a subject in need thereof, the method comprising implanting one or more magnetic screw devices into each of two or more vertebrae at the curvature, adjacent to the curvature, or a combination thereof, wherein each magnetic screw device comprises a fastening stem, a housing, a magnet assembly, and one or more magnets, wherein the fastening stem comprises a first end, a second end, a shank therebetween, and a longitudinal axis therebetween, wherein the first end comprises a spherical or part spherical surface, the second end comprises a taper to a pointed or approximately pointed shape, and the shank comprises a thread;

the housing comprises a top end, a bottom end, wall therebetween, and a bore between the top end and bottom end that defines an inner surface, wherein a portion of the inner surface adjacent to the bottom end comprises a concave spherical or part-spherical surface that is configured to engage with the spherical or part-spherical surface of the first end of the fastening stem; and wherein the housing comprises a first slot and a second slot that extends from the top end towards the bottom end and is located on opposing sites of the wall;

the magnet assembly comprises a shaft, a magnet holder on one or both ends of the shaft, a removable holder cap for each magnet holder, a longitudinal axis extending between the ends of the shaft, and a sleeve adjacent to each end of the shaft, wherein each magnet holder comprises an outer surface, a bore defining an inner surface, a closed end, and an open end; wherein each holder cap is configured to enclose the open end of the magnet holder; wherein the shaft is removably received by the first slot and second slot of the housing; and wherein the shaft is configured to extend between the first slot and the second slot of the housing;

and each magnet is configured to be received by one of the magnet holders.

20. A kit comprising:
(a) two or more constructs, wherein each construct comprises a fastening stem in connection with a housing;
(b) two or more magnet assemblies;
(c) two or more magnets; and
(d) instructions on how to assemble magnetic screw devices from the two or more constructs, magnet assemblies, and the two or more magnets; instructions on how to implant the magnetic screw devices into a subject; or a combination thereof;

wherein:
the fastening stem comprises a first end, a second end, a shank therebetween, and a longitudinal axis therebetween, wherein the first end comprises a spherical or part-spherical surface, the second end comprises a taper to a pointed or approximately pointed shape, and the shank comprises a thread;

the housing comprises a top end, a bottom end, a wall therebetween, and a bore between the top end and bottom end that defines an inner surface, wherein a portion of the inner surface adjacent to the bottom end comprises a concave spherical or part-spherical surface that is configured to engage with the spherical or part-spherical surface of the first end of the fastening stem; and wherein the housing comprises a first slot and a second slot that extends from the top end towards the bottom end and is located on opposing sites of the wall;

the magnet assembly comprises a shaft, a magnet holder on one or both ends of the shaft, a removable holder cap for each magnet holder, and a sleeve adjacent to each end of the shaft, wherein each magnet holder comprises an outer surface, a bore defining an inner surface, a closed end, and an open end; wherein each holder cap is configured to enclose the open end of the magnet holder; wherein the shaft of the magnet assembly is removably received by the first slot and second slot of the housing; and wherein the shaft is configured to extend between the first slot and the second slot of the housing; and each magnet is configured to be received by one of the magnet holders.

* * * * *